(12) United States Patent
Sagisaka et al.

(10) Patent No.: US 9,133,211 B2
(45) Date of Patent: Sep. 15, 2015

(54) DITHIENOBENZODITHIOPHENE SEMICONDUCTIVE MATERIAL AND ELECTRONIC DEVICE USING THE SAME

(75) Inventors: Toshiya Sagisaka, Kanagawa (JP); Satoshi Yamamoto, Kanagawa (JP); Takuji Kato, Fukuoka (JP); Takashi Okada, Kanagawa (JP); Masato Shinoda, Kanagawa (JP); Daisuke Goto, Kanagawa (JP); Shinji Matsumoto, Kanagawa (JP); Masataka Mohri, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 246 days.

(21) Appl. No.: 13/386,454

(22) PCT Filed: Jul. 15, 2010

(86) PCT No.: PCT/JP2010/062391
§ 371 (c)(1),
(2), (4) Date: Jan. 23, 2012

(87) PCT Pub. No.: WO2011/010710
PCT Pub. Date: Jan. 27, 2011

(65) Prior Publication Data
US 2012/0119195 A1    May 17, 2012

(30) Foreign Application Priority Data

Jul. 22, 2009 (JP) ................. 2009-171441
May 25, 2010 (JP) ................. 2010-119001

(51) Int. Cl.
| | | |
|---|---|---|
| H01L 51/30 | (2006.01) | |
| C07D 495/22 | (2006.01) | |
| H01L 51/00 | (2006.01) | |
| H01L 51/05 | (2006.01) | |

(52) U.S. Cl.
CPC .......... *C07D 495/22* (2013.01); *H01L 51/0074* (2013.01); *H01L 51/0541* (2013.01); *H01L 51/0545* (2013.01); *H01L 51/0558* (2013.01)

(58) Field of Classification Search
None
See application file for complete search history.

(56) References Cited

U.S. PATENT DOCUMENTS

| | | | |
|---|---|---|---|
| 7,166,689 B2 | 1/2007 | Sagisaka et al. | |
| 7,550,554 B2 | 6/2009 | Sagisaka et al. | |
| 7,816,674 B2 | 10/2010 | Kato et al. | |
| 2003/0047719 A1 | 3/2003 | Heeney et al. | |
| 2009/0261300 A1 | 10/2009 | Watanabe | |

FOREIGN PATENT DOCUMENTS

| | | |
|---|---|---|
| CN | 101523631 A | 9/2009 |
| EP | 2 067 782 A1 | 6/2009 |
| JP | 5 55568 | 3/1993 |
| JP | 2007 266411 | 10/2007 |
| JP | 2009021389 A * | 1/2009 |
| JP | 2009 54810 | 3/2009 |
| JP | 2009-059841 A | 3/2009 |
| JP | 2009 260287 | 11/2009 |
| WO | WO 2008/026602 A1 | 3/2008 |
| WO | 2010 000670 | 1/2010 |

OTHER PUBLICATIONS

Aleveque et al. "Effects of aromatic spacers on the properties of organic field effect transistors based on pi-extended tetrathiafulvalene derivatives" J. Mater. Chem. 2009, 19, 3648-3651. Date of on-line publication: Apr. 17, 2009.*
Machine translation of JP 2009-054810. Date of publication: Mar. 12, 2009.*
Machine translation of JP 2009-021389. Date of publication: Jan. 29, 2009.*
Bao, Z., et al., "Soluble and processable regioregular poly(3hexylthiopene) for thin film fieldeffect transitor applications with high mobility," Applied Physics Letters, vol. 69, pp. 4108-4110, (Oct. 23, 1996).
Sirringhaus, H., et al., "High-Resolution Inkjet Printing of All-Polymer Transitor Circuits," Science, vol. 290, pp. 2123-2126, (Dec. 15, 2000).
Ebata, H., et al., "Synthesis, Properties and Structures of Benzo[1,2-b:4,5-b']bis[b]benzothiophene and Benzo[1,2-b:4,5-b']bis[b]benzoselenophene," Organic Letters, vol. 9, No. 22, pp. 4499-4502, (2007).
Gao, P., et al., "Dithieno[2,3-d;2',3'-d']benzo[1,2-b;4,5-b']dithiophene (DTBDT) as Semiconductor for High-Performance, Solution-Processed Organic Field-Effect Transitors," Advanced Materials, vol. 21, pp. 213-216, (2009).
International Search Report Issued Sep. 7, 2010 in PCT/JP10/62391 Filed Jul. 15, 2010.

(Continued)

*Primary Examiner* — Andrew K Bohaty
(74) *Attorney, Agent, or Firm* — Oblon, McClelland, Maier & Neustadt, L.L.P.

(57) ABSTRACT

To provide an organic semiconductive material, expressed by the following general formula I: General Formula I where R1 to R10 are each independently a hydrogen atom, a substituted or unsubstituted alkyl group, a substituted or unsubstituted alkoxy group, a substituted or unsubstituted alkylthio group, or a substituted or unsubstituted aryl group, and may be bonded to each other to form a ring; and X is a carbon atom or a nitrogen atom.

13 Claims, 22 Drawing Sheets

(56) References Cited

OTHER PUBLICATIONS

Extended European Search Report issued Jun. 15, 2012 in European Patent Application No. 10802330.0.

Office Action issued Mar. 28, 2014 in Japanese Patent Application No. 2010-119001.

Combined Chinese Office Action and Search Report issued Feb. 8, 2014 in Patent Application No. 201080042231.9 with English Translation and English Translation of Category of Cited Documents.

* cited by examiner

DITHIENOBENZODITHIOPHENE SEMICONDUCTIVE MATERIAL AND ELECTRONIC DEVICE USING THE SAME

TECHNICAL FIELD

The present invention relates to a novel organic semiconductive material, which is effectively used as an organic electronics material.

BACKGROUND ART

Organic thin film transistors using organic semiconductive materials have been actively studied in recent years.

The organic semiconductive materials can be formed into a thin film by a simple wet process, such as printing and spin-coating. Therefore, they have advantages over thin film transistors using the conventional inorganic semiconductive material, such as the reduction in temperature for production processes.

Since use of the organic semiconductive material can reduce the temperature of the production processes, the thin film thereof can be formed on a plastic substrate which has generally low heat resistance. As a result, weights or costs of resulting electronics devices such as a display can be reduced, and various uses and applications thereof taking advantage of the flexible plastic substrate can be expected.

Some organic semiconductive materials have been proposed so far, such as poly(3-alkylthiophene) (see NPL 1), and a copolymer of dialkylfluorene and bithiophene (see NPL 2).

Since these organic semiconductive materials have some solubility to a solvent, though it is low, they can be formed into a thin film by coating or printing without using a technique such as vacuum deposition.

However, these polymer materials have restrictions in their purification methods. Therefore, some problems still remain. For example, it is complicated and time consuming to obtain a material of high purity, and quality of the material is not stable as there are variations in molecular weight or molecular weight distribution thereof.

Organic semiconductive materials of low molecular weight have also been proposed, such as acene materials (e.g. pentacene) (for example, see PTL 1).

It has been reported that the organic thin film transistor including an organic semiconductive layer formed of the aforementioned pentacene has relatively high electron mobility. However, these acene materials have extremely low solubility to common solvents. Therefore, these materials need to be vacuum-deposited to form a thin film thereof as an organic semiconductive layer of an organic thin film transistor. For this reason, these materials do not meet the demand in the art, which is to provide an organic semiconductive material that can be formed into a thin film by the aforementioned wet process such as coating or printing.

Moreover, there are some reports regarding low-molecular-weight organic semiconductive materials that have solubility to solvents. However, these materials still have problems. For example, a film formed of such material by a wet process is in the state of amorphous, and thus it is difficult to form a continuous film using such material due to crystal properties of the material. Moreover, properties of resulting elements formed of such material may vary, and desirable characteristics of the film cannot be obtained using such material.

In the case where the material has a crystal structure in which molecules are stacked by π-π interaction, such as the case of the dithienobenzothiophene derivative (see PTL2 and NPL 4), the crystals thereof tend to form needle shapes, and thus it may not be able to form a continuous thin film. In addition, the anisotropy of the charge transferring property may vary even within one crystal, and resulting elements formed using the material may largely vary. Accordingly, this material is not suitable for practical use. Especially, it should be noted that the crystal structure of the material (including the shape of the crystal) is difficult to assume based on the molecular structure of the material. Therefore, further improvements of organic semiconductive materials are still desired.

CITATION LIST

Patent Literature

[PTL1] Japanese Patent Application Laid-Open (JP-A) No. 05-55568
[PTL2] International Patent Application No. WO 10/000670

Non-Patent Literature
[NPL1] Appl. Phys. Lett., 69(26), 4108 (1996)
[NPL2] Science, 290, 2123 (2000)
[NPL3] Organic Letters, 2007, 9, 22, 4499
[NPL4] Advanced Materials, 2009, 21, 213-216

SUMMARY OF INVENTION

Technical Problem

In order to solve the aforementioned problems in the art, the present invention aims at providing an organic semiconductive material of excellent properties, which can be formed into a continuous film by two-dimensionally growing crystals thereof by a simple process such as coating, printing or deposition.

Solution to Problem

The present inventors conducted studies and researches to achieve the aforementioned object, and reached the following insights. Namely, the present invention has been made based on the insights that the problems in the art can be solved by introducing a certain modified group to a certain position of a molecule of the material.

Means for solving the aforementioned problems are as follows.
<1> An organic semiconductive material, expressed by the following general formula I:

General Formula I

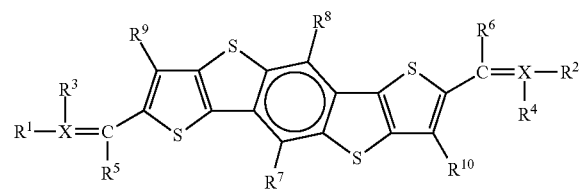

where $R^1$ to $R^{10}$ are each independently a hydrogen atom, a substituted or unsubstituted alkyl group, a substituted or unsubstituted alkoxy group, a substituted or unsubstituted alkylthio group, or a substituted or unsubstituted aryl group, and may be bonded to each other to form a ring; and X is a carbon atom or a nitrogen atom.

<2> The organic semiconductive material according to <1>, wherein $R^1$ and $R^2$ are each independently a substituted or unsubstituted alkyl group, a substituted or unsubstituted alkoxy group, a substituted or unsubstituted alkylthio group, or a substituted or unsubstituted aryl group.

<3> The organic semiconductive material according to <2>, wherein $R^1$ and $R^2$ are each independently a substituted or unsubstituted aryl group.

<4> The organic semiconductive material according to any one of <1> to <3>, wherein $R^1$ and $R^2$ are identical.

<5> The organic semiconductive material according to any one of <1> to <4>, wherein $R^3$ to $R^6$ are each independently a lower alkyl group or a hydrogen atom.

<6> The organic semiconductive material according to any one of <1> to <5>, wherein $R^3$ to $R^{10}$ are all hydrogen atoms.

<7> The organic semiconductive material according to any one of <1> to <4>, wherein $R^1$ and $R^3$ are bonded to each other to form a ring, and $R^2$ and $R^4$ are bonded to each other to form a ring.

<8> The organic semiconductive material according to <7>, wherein $R^1$ to $R^4$ are each independently a substituted or unsubstituted alkylthio group.

<9> A charge-transporting member, containing the organic semiconductive material as defined in any one of <1> to <8>.

<10> An organic electronic device, containing the charge-transporting member as defined in <9>.

<11> The organic electronic device according to <10>, wherein the charge-transporting member is an organic semiconductive layer, and the organic electronic device is an organic thin film transistor.

<12> The organic electronic device according to <11>, further containing:
a pair of a first electrode and a second electrode, both separated from each other with the organic semiconductive layer existing therebetween; and
a third electrode,
wherein a current running through' the organic semiconductive layer between the first electrode and the second electrode is controlled by adjusting the voltage applying to the third electrode.

<13> The organic electronic device according to <12>, further containing an insulating film between the third electrode and the organic semiconductive layer.

<14> A display device, containing:
a display element equipped with the organic electronic device as defined in any one of <11> to <13>,
wherein the display element is driven by the organic electronic device.

<15> The display device according to <14>, wherein the display element is at least one selected from the group consisting of a liquid crystal element, an electroluminescence element, an electrochromic element, and an electrophoretic element.

Advantageous Effects of Invention

The present invention provides an organic semiconductive material of excellent properties, which can be formed into a continuous film by two-dimensionally growing crystals thereof by a simple process such as coating, printing, or the like.

DESCRIPTION OF EMBODIMENTS

Figure 1A:
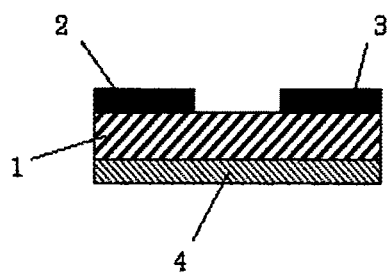
FIGS. 1A to 1D are schematic structural diagrams showing examples of an organic thin film transistor, as examples of the organic electronic device of the present invention.

The present invention will be specifically explained hereinafter.

The molecular structure of the organic semiconductive material of the present invention will be explained first.

The organic semiconductive material has the structure expressed by the following general formula I.

General Formula I

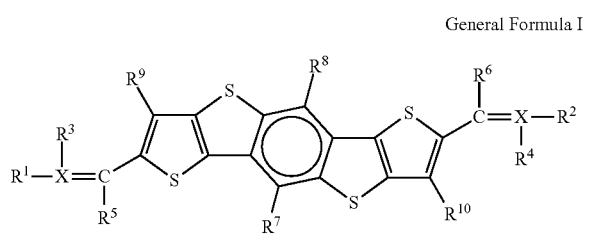

In the general formula I, $R^1$ to $R^{10}$ are each independently a hydrogen atom, a substituted or unsubstituted alkyl group, a substituted or unsubstituted alkoxy group, a substituted or unsubstituted alkylthio group, or a substituted or unsubstituted aryl group, and may be bonded to each other to form a ring; and X is a carbon atom or a nitrogen atom.

Examples of the substituted or unsubstituted alkyl group expressed as $R^1$ to $R^{10}$ include a methyl group, an ethyl group, a n-propyl group, an i-propyl group, a t-butyl group, a s-butyl group, a n-butyl group, an i-butyl group, a pentyl group, a hexyl group, a heptyl group, an octyl group, a nonyl group, a decyl group, an undecyl group, a dodecyl group, a 9-heptadecyl group, 3,7-dimethyloctyl group, a 2-ethylhexyl group, a trifluoromethyl group, a 2-cyanoethyl group, a benzyl group, a 4-chlorobenzyl group, a 4-methylbenzyl group, a cyclopentyl group, and a cyclohexyl group. These may be bonded to each other to form a ring. Among them, $R^3$, $R^4$, $R^5$, and $R^6$ are each preferably a lower alkyl group or a hydrogen atom, more preferably a hydrogen atom, as the molecular structure may be distorted when $R^3$, $R^4$, $R^5$, and $R^6$ have bulky structures. For the same reason, the spatial arrangement of the double bond present at both terminals of dithienobenzodithiophene is preferably trans. Examples of the substituted or unsubstituted alkoxy group and the substituted or unsubstituted alkylthio group include alkoxy groups and alkyothio groups in which an oxygen atom or sulfur atom is introduced to various positions of the aforementioned alkyl groups.

As a result of the improvement in the solubility of the organic semiconductive material, it is possible to form a film thereof by a wetting process in the course of productions of devices such as an organic EL element, and organic transistor element. For example, the material with high solubility allows wide selections of a coating solvent, wide temperature range for the preparation of a coating solution, and wide temperature and pressure ranges for drying the solvent. The material with such high processibility is most likely to provide a thin film of high purity, uniformity and quality.

Specific examples of the substituted or unsubstituted aryl group expressed as $R^1$ to $R^{10}$ include a benzene group, a naphthalene group, a biphenyl group, a terphenyl group, a quarterphenyl group, a pyrene group, a fluorene group, a 9,9-dimethylfluorene group, an azulene group, an anthracene group, a triphenylene group, a chrysene group, a 9-benzylidenefluorene group, a 5H-dibenzo[a,d]cycloheptene group, a [2,2]-paracyclophane, a triphenylamine group, a thiophene group, a bisthiophene group, a terthiophene group, a quaterthiophene group, a thienothiophene group, a benzothiophene group, a dithienylbenzene group, a furan group, a benzofuran group, a carbazole group, a benzodithiazol group, a pyridine group, and a quinoline group. These may be further substituted with the aforementioned substituted or unsubstituted alkyl, alkoxy group, thioalkoxy group, or a halogen group such as a fluorine atom, chlorine atom, iodine atom, bromine atom, and the like.

It has been found by the present inventors that a crystalline continuous film of the material can be easily formed by introducing the aforementioned aryl groups at $R^1$ and $R^2$, as the vinylene-aryl moieties present at both terminals of the dithienobenzodithiophene moiety are interacted to the adjacent molecules in the manner of CH-π interaction within a crystal of the material, which allows crystals of the material to easily grow two-dimensionally. In the case where the aryl groups are introduced at the aforementioned positions, a conjugated system of the molecule is enlarged, and thus an ionic potential of the material becomes low. As a result, a hole-transporting ability of the material is improved. Moreover, it is possible to improve the electron transferring property of the material by introducing an electron-withdrawing substituent to the aforementioned aryl group, as the aryl group is bonded to the dithienobenzodithiophene moiety via a double bond. In addition, the molecular modification in such manner can significantly improve heat resistance of the material.

A production method of the organic semiconductive material of the present invention will be explained next.

A method for synthesizing the organic semiconductive material can be suitably selected from various methods known in the art without any restriction. For example, the organic semiconductive material can be synthesized by forming a dithiobenzodithiophene structure, and then forming double bond sites at both ends thereof. Alternatively, it may be synthesized by forming a dithiobenzodihiophene structure after introducing double bond sites at the both ends thereof.

When the organic semiconductive material is synthesized by forming a dithiobenzodithiophene structure, and then forming double bond sites at both ends thereof, Wittig-Horner reaction, Wittig reaction, Heck reaction, Suzuki-Miyaura coupling reaction or the like can be used, where the Wittig-Horner reaction uses a carbonyl compound and phosphonate, the Witting reaction uses a carbonyl compound and a phosphonium salt, the Heck reaction uses a vinyl substitution product and halide, and the Suzuki-Miyaura coupling reaction uses a vinylboronic acid derivative and halide.

The Wittig-Horner reaction and Wittig reaction are particularly effective because their reaction processes are simple. As an example of the synthesis method, a method for producing the organic semiconductive material using the Wittig-Horner reaction will be explained.

The organic semiconductive material is obtained by mixing base and a solution in which a phosphonic ester compound and a carbonyl compound are present, as described in the following reaction formula:

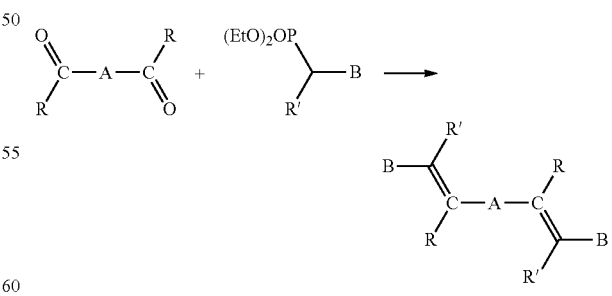

The aforementioned carbonyl compound can be synthesized by various reactions known in the art. Examples thereof include Vilsmeier reaction, a reaction of an aryl lithium compound with a formulation or acylation reagent (e.g. DMF, N-formylmorpholine, N-formylpiperidine, various acid chlorides, and various acid anhydrides), Gatterman reaction, and various oxidation reactions of the hydroxyl compound shown below. A desirable carbonyl compound can be synthesized by these reactions.

Vilsmeier Reaction:

Reaction of an Aryl Lithium Compound with a Formulation or Acylation Reagent:

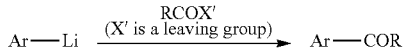

Gatterman Reaction:

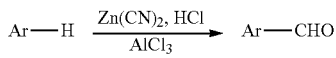

Oxidation Reaction of the Hydroxyl Compound:

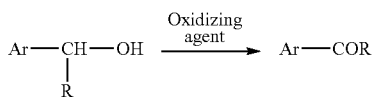

Moreover, the aforementioned sulfonic ester compound can be also synthesized by various reactions known in the art, but the below-presented Michaelis-Arbuzov reaction is particularly preferable because the reaction process thereof is simple.

Michaelis-Arbuzov Reaction:

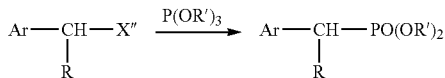

X" is halogen

The base used for the aforementioned reaction is suitably selected depending on the intended purpose without any restriction, provided that it forms a phosphonate carboanion. Examples thereof include metal alkoxides, metal hydrides, and organic lithium compounds, and specific examples thereof include potassium t-butoxide, sodium t-butoxide, lithium t-butoxide, potassium 2-methyl-2-butoxide, sodium 2-methyl-2-butoxide, sodium methoxide, sodium ethoxide, potassium ethoxide, potassium methoxide, sodium hydride, potassium hydride, methyl lithium, ethyl lithium, propyl lithium, n-butyl lithium, s-butyl lithium, t-butyl lithium, phenyl lithium, lithium naphthalide, lithium amide, and lithium diisopropyl amide.

An amount of the base used for the reaction is generally the same to the amount of the phosphonic ester, but the larger amount thereof may be used without adversely affecting the reaction.

When the dithienobenzothiophene structure is formed after introducing double bonds to form an organic semiconductive material, the organic semiconductive material can be synthesized in the manner described below.

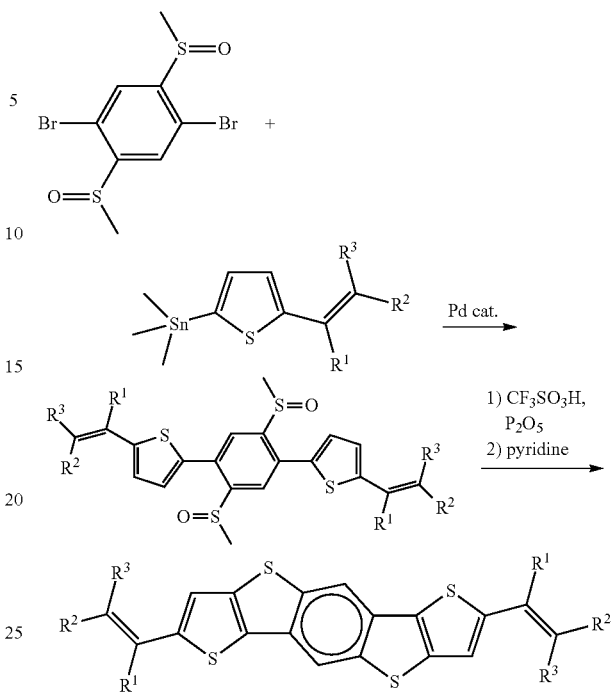

The organic semiconductive material obtained in the aforementioned manner is used after removing impurities such as catalysts and/or inorganic salts-used in the reaction, the remaining non-reacted materials, and by-product(s).

Various methods known in the art can be used for purifying the organic semiconductive material, and such methods include various chromatographic methods, sublimation purification, reprecipitation, extraction, Soxhlet extraction, ultrafiltration, and dialysis.

It is preferred that the organic semiconductive material be formed to have a purity as high as possible, as the impurities may adversely affect semiconductor properties of the material. The organic semiconductive material having excellent solubility does not have many restrictions in a purification method thereof. Such purification method of wide margin gives favorable influence to the semiconductor properties thereof.

The organic semiconductive material obtained in the aforementioned method is dissolved in a solvent, and the resulting solution is applied onto a substrate to form a thin film. For example, dichloromethane, tetrahydrofuran, chloroform, toluene, dichlorobenzene, xylene, and the like are used as the solvent.

Examples of the method for forming a film include spin-coating, casting, dipping, inkjet printing, doctor-blade coating, screen printing, and dispensing. The thin film of the organic semiconductive material can be formed by any wet film-forming process known in the art.

Moreover, it is possible to make the organic semiconductive material into a crystal plate or thick film by casting or the like. The film-forming method, solvent for use, or combination thereof is appropriately selected from those mentioned above depending on a device to be produced.

Furthermore, the organic semiconductive material can also be formed into a film by a dry process such as vacuum-deposition.

The thin film, thick film, or crystal of the organic semiconductive material formed in the aforementioned manners functions as a charge-transferring member for various functional devices, such as a photoelectric transducer, thin-film transistor element, light-emitting device, and thus various electronic devices can be produced by using the organic semiconductive material of the invention.

An Organic thin-film transistor will be explained with reference to schematic structural diagrams of FIGS. 1A to 1D, as examples of the organic electronic device of the present invention.

The organic thin-film transistor has an organic semiconductive layer 1 containing the compound expressed by the general formula I, as a main component.

The organic thin-film transistor further contains a first electrode (i.e. a source electrode) 2 and a second electrode (i.e. a drain electrode) 3 both separately provided with the organic semiconductive layer 1 existing between them, and a third electrode (i.e. a gate electrode) 4 facing the first and second electrodes. Note that, an insulating film 5 may be formed between the gate electrode 4 and the organic semiconductive layer 1. In the organic thin-film transistor, an electric current running through the portion of the organic semiconductive layer 1 between the source electrode 2 and the drain electrode 3 is controlled by adjusting the voltage applied to the gate electrode 4.

The organic thin-film transistor is formed on a predetermined substrate. The material of the substrate is suitably selected from substrate materials known in the art, and examples thereof include glass, silicon, and plastic. When a conductive substrate is used as the aforementioned substrate, the conductive substrate can also function as the gate electrode 4.

Moreover, the organic thin-film transistor may have the structure in which the gate electrode 4 and the conductive substrate are laminated. In the case where the organic thin-film transistor is applied for a device, a plastic sheet is preferably used as the substrate from the stand point of obtaining excellent practical properties, such as light weight, low cost, and shock resistance.

Examples of the plastic sheet include films of polyethylene terephthalate, polyethylene naphthalate, polyethersulfone, polyetherimide, polyether ether ketone, polyphenylene sulfide, polyacrylate, polyimide, polycarbonate, cellulose triacetate, celluloseacetate propionate, and the like.

The structural elements of the organic thin-film transistors of FIGS. 1A to 1D, other than the aforementioned organic semiconductive layer, will be explained hereinafter.

The organic semiconductive layer 1 is formed so as to be in contact with the first electrode (i.e. the source electrode), the second electrode (i.e. the drain electrode), and optionally the insulating film 5.

The insulating film 5 will be explained below.

The insulating film used in the organic thin-film transistor can be formed by using various insulating materials.

Examples of the insulating material include inorganic insulating materials such as silicon oxide, silicon nitride, aluminum oxide, aluminum nitride, titanium oxide, tantalum oxide, tin oxide, vanadium oxide, barium strontium titanate, barium zirconate titanate, lead zirconate titanate, lanthanum lead titanate, strontium titanate, barium titanate, magnesium barium fluoride, bismuth tantalate niobate, and yttrium trioxide.

Examples thereof also include polymer compounds such as polyimide, polyvinyl alcohol, polyvinyl phenol, polyester, polyethylene, polyphenylene sulfide, polystyrene, polymethacrylate, unsubstituted or halogen-substituted polyparaxylylene, polyacrylonitrile, and cyanoethyl pullulan.

Moreover, two or more insulating materials may be used in combination. Among the aforementioned insulating materials, preferable materials are ones having high dielectric constant and low conductivity, not limited to the specific materials.

Examples of the method for forming the insulating film 5 include: dry methods such as CVD, plasma CVD, plasma polymerization, and deposition; and wet processes such as spray-coating, spin-coating, dip-coating, inkjet-printing, casting, blade-coating, and bar-coating.

The interface modification between the organic semiconductive layer 1 and the insulating film 5 will be explained next.

An organic thin film may be formed between the organic semiconductive layer 1 and the insulating film 5 for the purpose of improving the adhesion between the insulating film 5 and the organic semiconductive layer 1, as well as reducing the driving voltage or leak current of the organic thin-film transistor.

The organic thin film does not have any restriction in any way, provided that it does not chemically affect the organic semiconductive layer. For example, an organic molecular film or organic polymer film can be used as the organic thin film.

Example of the organic molecular film include a film formed of a coupling agent such as octadecyltrichlorosilane, and hexamethyldisilazane.

The organic polymer film may be formed of any of the aforementioned insulating polymer materials, and can also function as one of insulating layers.

Moreover, the organic thin film may be subjected to an anisotropic treatment, such as rubbing.

The electrodes contained in the organic thin-film transistor will be explained next.

The organic thin-film transistor contains the first electrode (i.e. the source electrode) and the second electrode (i.e. the drain electrode) both separately provided with the organic semiconductive layer exiting between these electrodes, and the third electrode (i.e. the gate electrode) configured to control the current running through the portion of the organic semiconductive layer present between the first and second electrode.

Since the organic thin-film transistor is a switching element, it is important that the state of the applied voltage to the third electrode (i.e. the gate electrode) can largely influence on the amount of the current running between the first electrode (i.e. the source electrode) and the second electrode (i.e. the drain electrode). This means that a large amount of a current runs when the transistor is in the driven state, and no current runs in the undriven state.

The gate electrode and the source electrode are suitably selected depending on the intended purpose without any restriction, provided that they are formed of a conductive material. Examples of the conductive material include: metals such as platinum, gold, silver, nickel, chromium, cupper, iron, tin, antimony, lead, tantalum, indium, aluminum, zinc, and magnesium; alloys such as alloys of the aforementioned metals; conductive metal oxides such as indium zinc oxide; and inorganic or organic semiconductor having the conductivity improved by doping or the like, where examples of inorganic or organic materials used for such inorganic or organic semiconductor include silicon monoclystal, polysilicon, amorphous silicon, germanium, graphite, polyacetylene, polyparaphenylene, polythiophene, polypyrrole, polyaniline, polythienylenevinylene, polyparaphenylenevinylene, and a complex compound of polyethylenedioxythiophene and polystyrene sulfonic acid.

It is preferred that the source electrode and drain electrode each have low electric resistance at the contact plane thereof with the semiconductive layer. Examples of the formation method of the aforementioned electrode include a method in which a thin conductive film is formed by deposition or sputtering using the aforementioned materials for the electrode as a raw material, and the thin conductive film is formed into a shape of an electrode by conventional lithographic process or lift-off process.

Moreover, the examples include a method in which a resist film is formed on a metal leaf of aluminum, cupper, or the like by thermal transferring or inkjet, and the metal leaf is etched using the resist film as a mask to obtain the desired electrode.

Furthermore, the electrode may be formed by applying a conductive polymer solution or dispersion liquid, or conductive particle dispersion liquid by inkjet so as to directly pattern the electrode, or the electrode may be formed from a coating layer by lithography or laser abrasion.

Alternatively, the electrode may be formed by patterning an ink containing conductive polymer or conductive particles, or conductive paste by printing such as relief printing, intaglio printing, and screen printing.

The organic thin film transistor optionally contains an extraction electrode for each electrode.

Moreover, the organic thin film transistor optionally contains a protective layer for protecting the transistor from physical damages, moisture or gas, or for the protection considering integration of the device, though the organic thin film transistor can be stably driven in the air.

The organic thin transistor is suitably used as an element for driving various conventional display elements such as a liquid crystal element, electroluminescence element, electrochromic element, and electrophoretic element, and by integrating these elements, a display, what is called "electric paper" can be produced.

The display device includes liquid crystal display elements in the case of a liquid display device, organic or inorganic electroluminescence display elements in the case of an EL display device, and electrophoresis display elements in the case of an electrophoresis display device, and a plurality of such display elements are aligned in the form of matrix in X direction and Y direction to construct the display device using the aforementioned display element as one display picture element (i.e. one pixel).

The display element is equipped with the organic thin film transistor as a switching element for applying voltage or supplying a current to the display element. The display device includes the same number of the switching elements to the number of the display element, i.e. the number of the display picture elements (i.e., the pixels).

The display element contains, other than the switching elements, members such as a substrate, an electrode (i.e. a transparent electrode), a polarizer, and a color filter. These members are suitably selected from those known in the art depending on the intended purpose without any restriction.

When the display device forms a certain image, only certain switching elements selected from all the switching elements provided in the matrix form turn on or off for applying voltage or a current to the corresponding display elements. When voltage or a current is not applied to the display elements, all the switching elements remain the state of ON or OFF. The display device can display the image at high speed and high contrast by having such configuration.

Note that, the display device displays an image by the conventional display operation known in the art.

For example, in the case of the liquid display element, the molecule alignments of the liquid crystals are controlled by applying voltage to the liquid crystals, to thereby display an image or the like.

In the case of the organic or inorganic electroluminescence display element, a current is supplied to a light-emitting diode formed of an organic material or inorganic material to emit the organic or inorganic film, to thereby display an image or the like.

In the case of the electrophoresis display element, voltage is applied to white coloring particles and black coloring particles each charged with the opposite polarity to each other to make the coloring particles electrically migrate in a certain direction. As a result, an image or the like is displayed.

The display device can be produced by a simple process, such as a process of coating or printing the switching element, can use as a substrate, and a plastic substrate or paper that does not have sufficient resistance to a high temperature processing. Moreover, the display device having a large area can be produced at low energy and cost, as the switching elements can be formed at low energy and cost.

In addition, a plurality of the organic thin film transistors can be integrated to form an IC, and such IC can be used as a device such as an IC tag.

EXAMPLES

The present invention will be specifically explained through Examples, hereinafter. The present invention shall not be construed as to limit the scope of the present invention. In Examples and Comparative Examples below, IR was measured by Spectrum GX FT-IR System manufactured by Perkin Elmer Co., Ltd., NMR was measured by JNM-ECX500 manufactured by JEOL Ltd., a mass spectrum was measured by LCT premier XE ASAP probe manufactured by Nihon Waters K.K., a melting point was measured by SSC/5200 DSC120 manufactured by Seiko Instruments Inc., a thermal decomposition temperature was measured by SSC5200 TG/DTA 220 manufactured by Seiko Instruments Inc., and ionization potential was measured by AC2 manufactured by Riken Keiki Co., Ltd.

Example 1

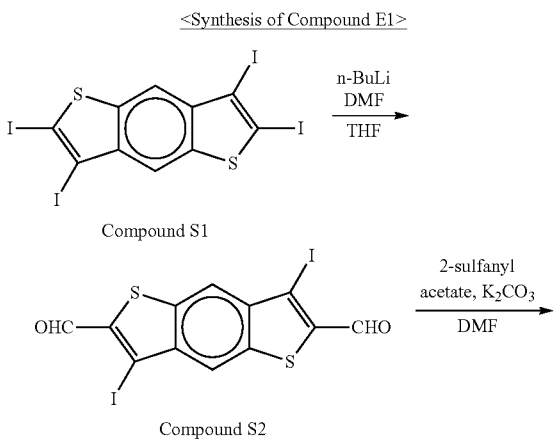

-continued

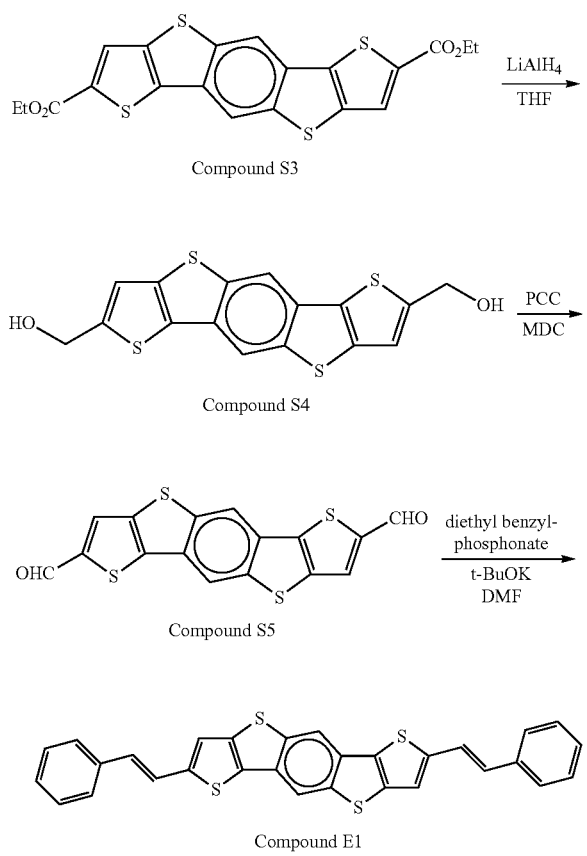

Compound S3

Compound S4

Compound S5

Compound E1

Compound E1 was synthesized through the above-presented synthesizing reactions.

Into a 100 mL flask, 0.743 g (1.071 mmol) of Compound S1, which had been synthesized in the method described in Organic Letters, 2007, 9, 22, 4499 (NPL 3), was added and then the inner atmosphere of the flask was replaced with argon gas. Thereafter, 70 mL of THF was added to the flask, followed by cooling down to −78° C.

To this solution, 1.41 mL (2.249 mmol) of a n-BuLi hexane solution (1.59 M) was added, and the mixture was stirred at −78° C. for 1 hour. Then, 4 mL of DMF was further added to the solution, followed by stirring at −78° C. for 1 hour. After adding diluted hydrochloric acid to the solution, the temperature thereof was returned to room temperature.

Water was then added to the solution. Thereafter, precipitated solids in the solution were removed by filtration, followed by washing with water, and methanol, respectively.

The thus obtained yellow solids were dried under reduced pressure, to thereby obtain 0.477 g of Compound S2. The yield thereof was 89%.

1H NMR (500 MHz, DMF-d7, TMS) δ/ppm: 8.99 (2H, s), 10.24 (2H, s) IR (KBr) v/cm$^{-1}$: 1660 (vC=O)

Into a 100 mL flask, 2.36 g (4.74 mmol) of Compound S2, 37 mL of DMF, 1.76 g (12.70 mmol) of potassium carbonate, and 1.05 mL (9.58 mmol) of ethyl thioglycolate were added, and the mixture was stirred at room temperature for 48 hours.

This reaction solution was dropped in water, and the precipitated solids in water were removed by filtration, followed by washing with water, and ethanol, respectively.

The obtained yellowish white solids were dried under reduced pressure, to thereby obtain 2.01 g of Compound S3. The yield thereof was 90%.

1H NMR (500 MHz, CDCl$_3$, TMS) δ/ppm: 1.44 (6H, t, J=7.1 Hz), 4.43 (4H, q, J=6.9 Hz), 8.04 (2H, s), 8.37 (2H, s). IR (KBr) v/cm$^{-1}$: 1712 (vC=O)

Into a 100 mL flask, 1.62 g (3.61 mmol) of Compound S3 was added. After replacing the inner atmosphere of the flask with argon gas, 40 mL of THF was added thereto.

The solution was cooled down to 0° C., and 0.62 g (16.3 mmol) of litium aluminum hydride was added to the cooled solution little by little. Then, the mixture was stirred at room temperature for 10 hours.

The mixture was then cooled to 0° C., and ethanol and diluted hydrochloric acid were added thereto. Then, the precipitated solids therein were removed by filtration.

After washing the solids with diluted hydrochloric acid, water, and then ethyl acetate, the solids were dried under reduced pressure, to thereby obtain 0.75 g of Compound S4 as colorless solids. The yield thereof was 57%.

1H NMR (500 MHz, CDCl$_3$, TMS) δ/ppm: 1.44 (6H, t, J=7.1 Hz), 4.43 (4H, q, J=6.9 Hz), 8.04 (2H, s), 8.37 (2H, s). IR (KBr) v/cm$^{-1}$: 3392 (vO-H)

Into a 25 mL flask, 50.0 mg (0.138 mmol) of Compound S4, and 0.690 g (0.690 mmol) of PCC carried on alumina (1 mmol/g) were added. After replacing the inner atmosphere of the flask with argon gas, 2 mL of dichloromethane was added thereto, and the mixture was stirred at room temperature for 2 days.

The solution was taken out by decantation, and the solvent was removed from the solution to thereby obtain Compound S5 as yellow solids.

1H NMR (500 MHz, DMSO-d6, TMS) δ/ppm: 8.54 (2H, s), 9.02 (2H, s), 10.08 (2H, s).

Into a 1,000 mL flask, 0.750 g (2.092 mmol) of Compound S5, and 3.820 g (16.74 mmol) of diethylbenzyl phosphonate were added thereto. After the inner atmosphere of the flask was replaced with argon gas, 500 mL of DMF was added thereto.

To this solution, 1.878 g (16.74 mmol) of t-BuOK was gradually added, and the mixture was stirred at 70° C. for 2 hours.

Figure 2:
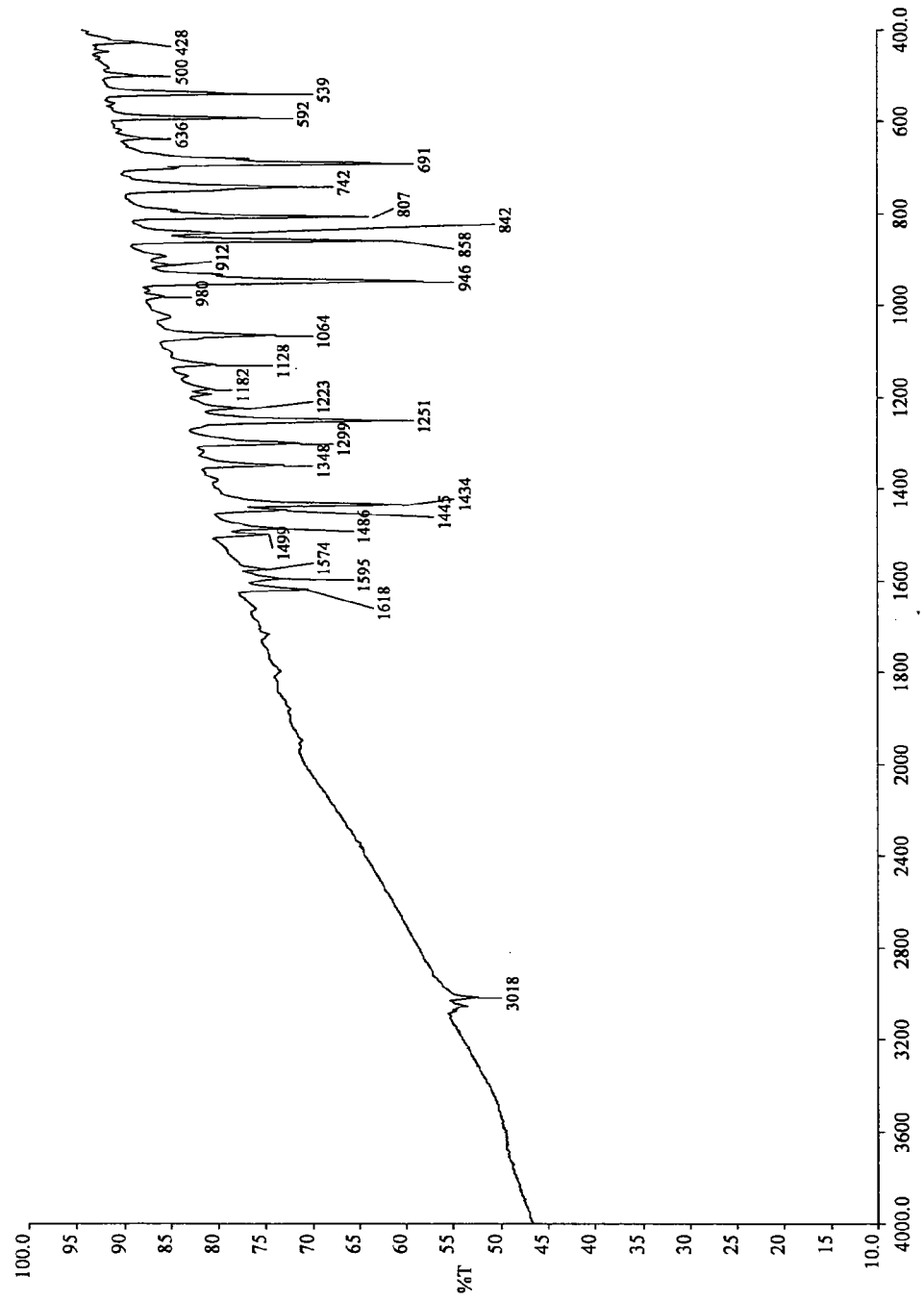
FIG. 2 is a graph showing an IR absorption spectrum of Compound E1 synthesized in Example 1.
Figure 3:
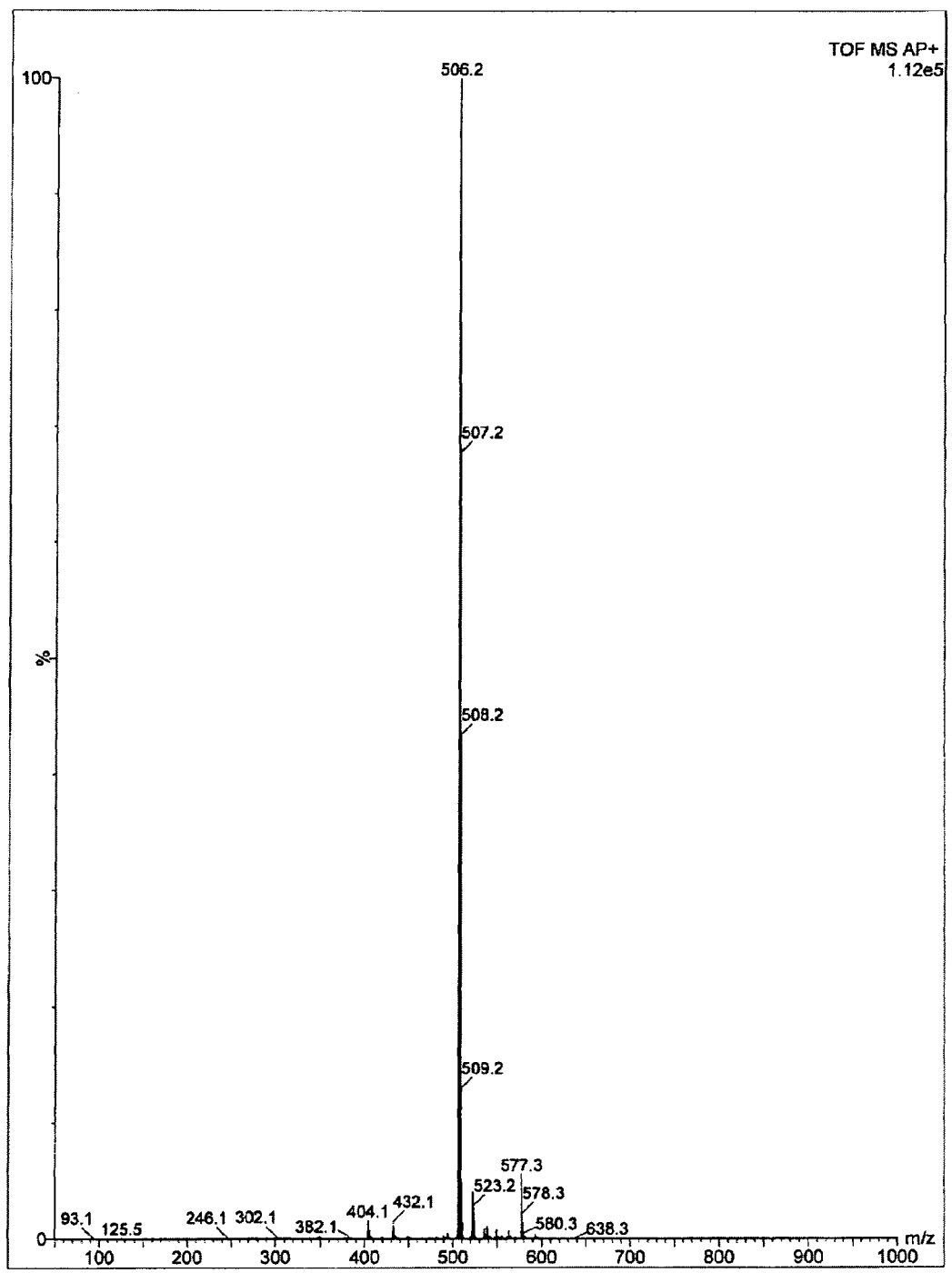
FIG. 3 shows a mass spectrum of Compound E1 synthesized in Example 1.

After removing DMF from the mixture under reduced pressure, the residue was respectively washed with water, methanol, hexane, and ethyl acetate, in this order. The obtained yellow solids were dried under reduced pressure, to thereby obtain 0.695 g of Compound E1. Compound E1 had a melting point of 362° C., and a thermal decomposition temperature of 416° C. An IR absorption spectrum of Compound E1 is shown in FIG. 2, and a mass spectrum of Compound E1 is shown in FIG. 3.

As a result of manufacturing a single crystal of the compound E1 by vapor phase growth, tabular crystals were obtained.

As a result of single crystal X-ray structure analysis using the crystals obtained above, it was found that it was the herringbone packing based on the intermolecular CH-π interaction.

Example 2

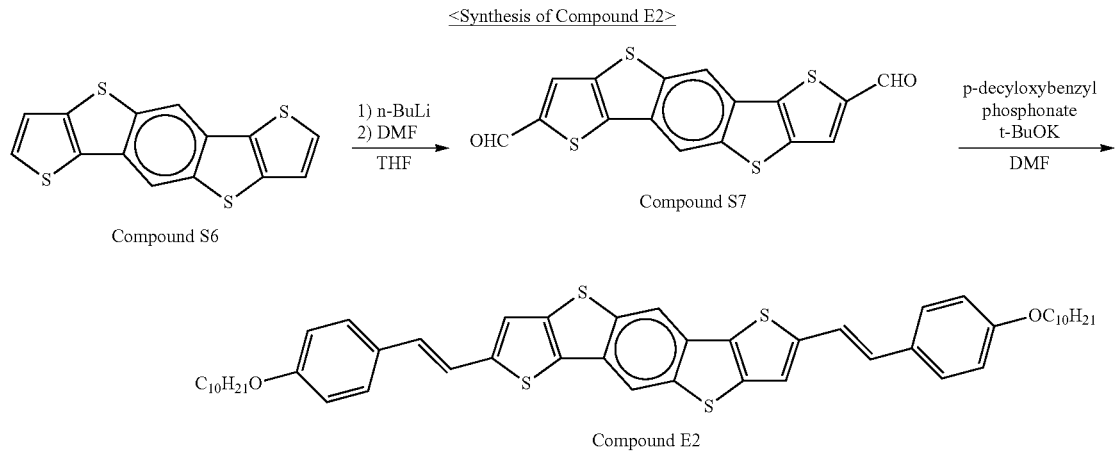

<Synthesis of Compound E2>

Compound E2 was synthesized through the above-presented reactions.

Into a 100 mL flask, 0.500 g (1.653 mmol) of Compound S6 (having a sublimation point of 200° C., and a melting point of 305° C.), which had been synthesized in accordance with the method described in Advanced Materials, 2009, 21, 213-216 (NPL 4), was added. After replacing the inner atmosphere of the flask with argon gas, 30 mL of THF was added thereto.

The obtained solution was cooled down to −20° C., and then 4.133 mmol of a n-BuLi hexane solution was dropped. The mixture was then stirred for 1 hour.

The mixture was further cooled down to −78° C., 2.5 mL of DMF was added thereto, followed by stirring for 30 minutes. After adding diluted hydrochloric acid to the mixture, the temperature thereof was returned to room temperature.

The precipitated solids therein were then removed by filtration, followed by washing respectively with water, ethanol, and ethyl acetate.

The solids were then dried under reduced pressure, to thereby obtain 0.392 g of Compound S7. The yield thereof was 66%.

Figure 4:
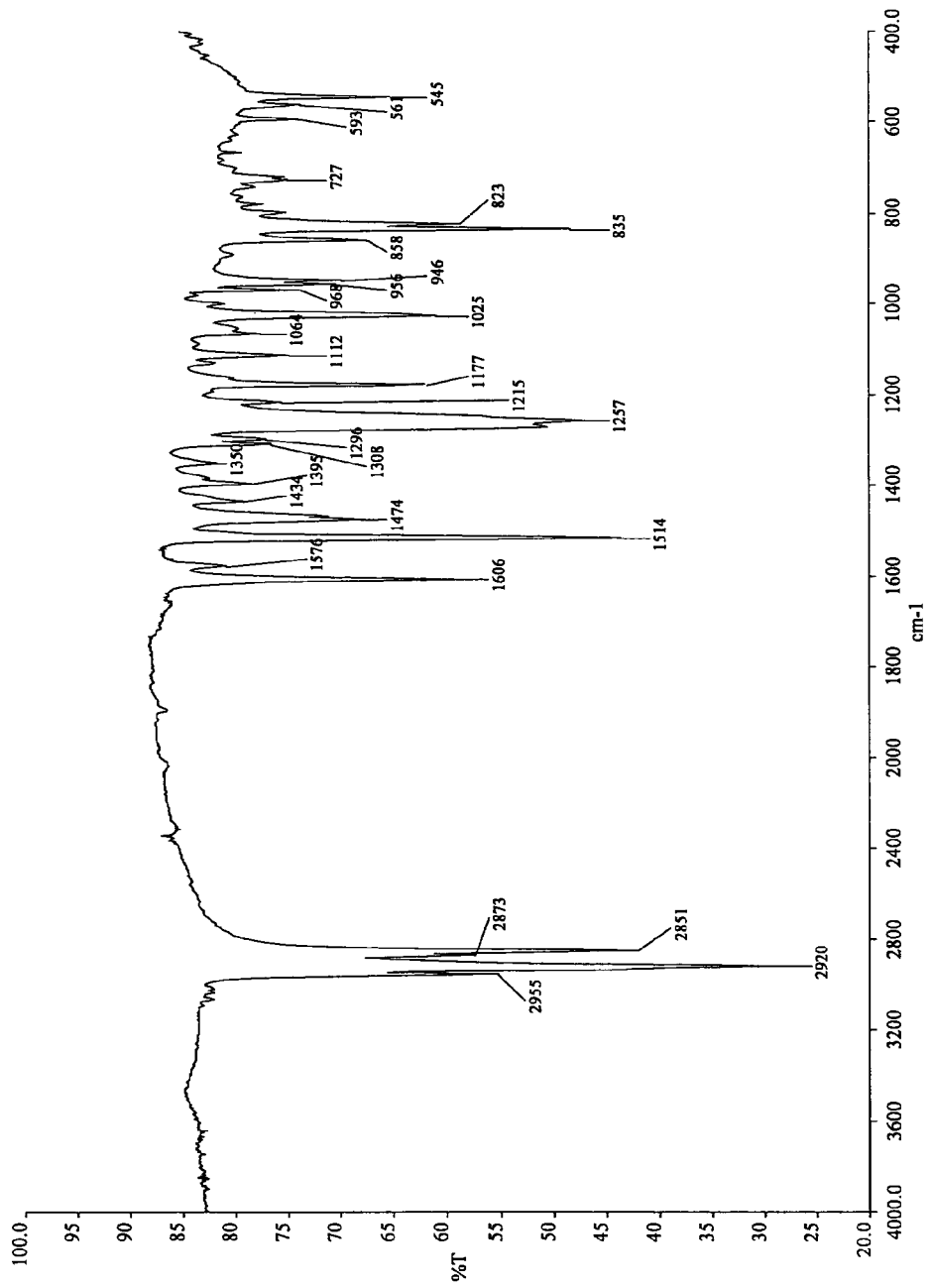
FIG. 4 is a graph showing an IR absorption spectrum of Compound E2 synthesized in Example 2.
Figure 5:
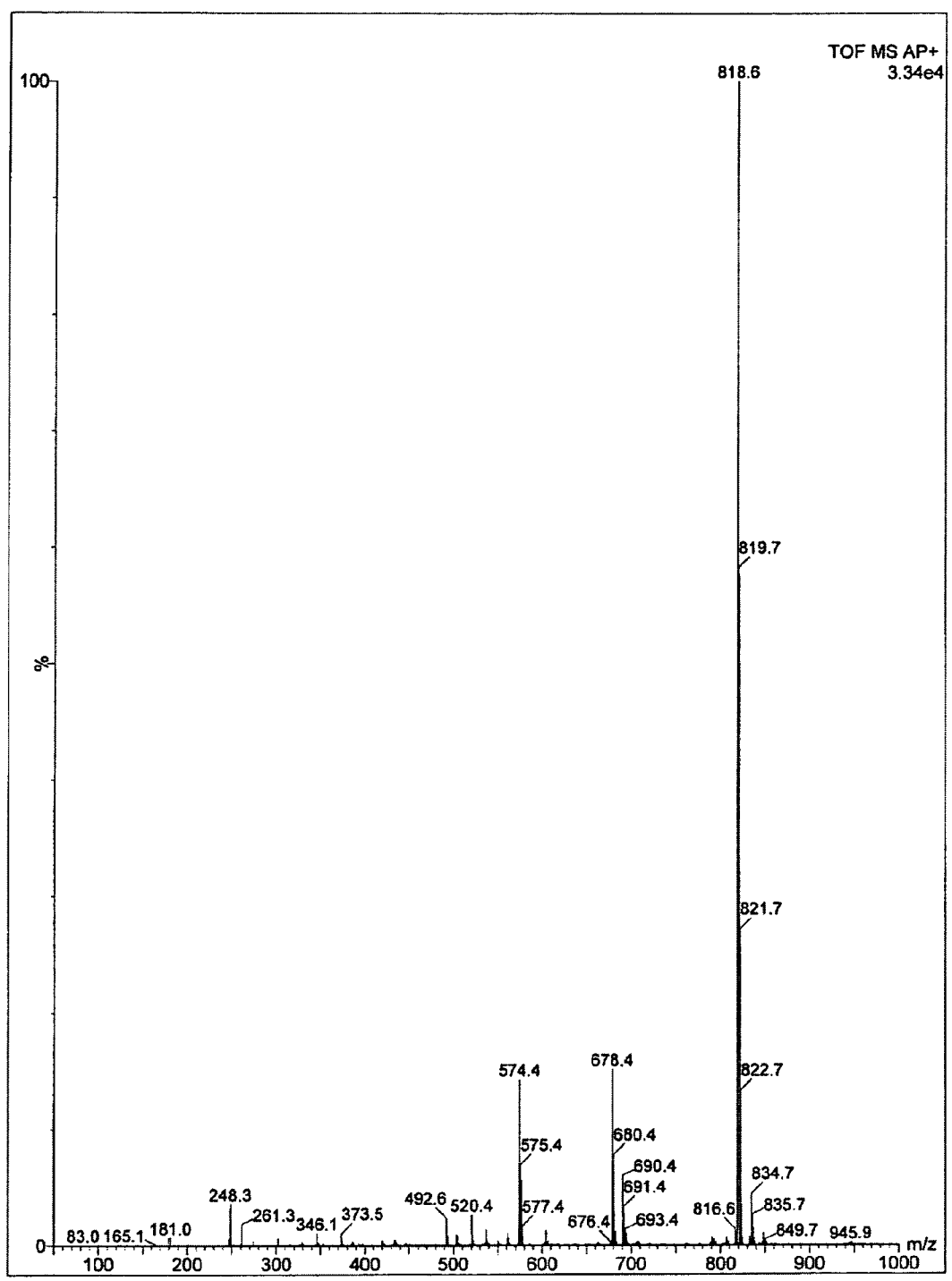
FIG. 5 shows a mass spectrum of Compound E2 synthesized in Example 2.

Compound E2 was prepared in the same manner as in Example 1, using the above-obtained Compound S7 and 4-decyloxyldiethylbenzyl phosphonate. Compound E2 had a thermal decomposition temperature of 394° C. An IR absorption spectrum of Compound E2 is shown in FIG. 4, and a mass spectrum of Compound E2 is shown in FIG. 5.

Example 3

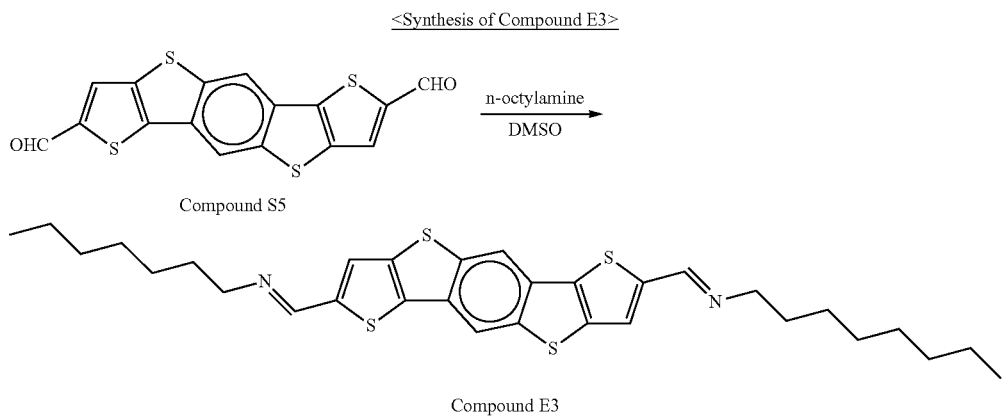

<Synthesis of Compound E3>

Compound E3 was synthesized through the above-presented reaction.

Into 100 ml flask, 0.500 g (1.395 mmol) of Compound S5 (an intermediate product just before Compound E1) synthesized in Example 1, 0.541 g (4.184 mmol) of n-octyl amine, and 30 mL of DMSO were added, and the mixture was stirred at room temperature for 12 hours. To this mixture, water was added, and the precipitated yellow solids therein were removed by filtration, followed by washing with ethanol. The solids were then purified by column chromatography, to thereby obtain 0.29 g of Compound E3 as yellow crystals.

1H NMR (500 MHz, CDCl$_3$, TMS) δ/ppm: 0.88 (6H, t, J=6.6 Hz), 1.2-1.4 (20H, m), 1.72 (4H, quint, J=6.88 Hz), 3.63 (4H, t, J=6.88 Hz), 7.49 (2H, s), 8.28 (2H, s), 8.43 (2H, s).

Example 4

<Preparation of Organic Thin Film Transistor>

A field-effect transistor having the structure shown in FIG. 1D was prepared using Compound E1 synthesized in Example 1, in the following manner.

A N-doped silicon substrate having a 300 nm-thick thermal oxide film was immersed in concentrated sulfuric acid for 24 hours, followed by washing.

The washed silicon substrate was immersed in a toluene solution of a silane coupling agent (n-octyltrichlorosilane) (1 mM), and was subjected to an ultrasonic treatment for 5 minutes, to thereby form a monomolecular film on the surface of the silicon oxide film.

To the obtained substrate, Compound E1 (which had been subjected to sublimation purification) obtained in Example 1 was vacuum-deposited (back pressure: up to $10^{-4}$ Pa, deposition rate: 0.1 Å/s, substrate temperature: 150° C., semiconductive film thickness: up to 50 nm), to thereby form an organic semiconductive layer.

Gold was then vacuum-deposited (back pressure: up to $10^{-4}$ Pa, deposition rate: 1 Å/s to 2 Å/s, film thickness: 50 nm) on the organic semiconductive layer using a shadow mask, to thereby form a source electrode and a drain electrode (channel length: 50 μm, channel width: 2 mm). The semiconductive layer and silicon oxide film were scraped off from the portion where no electrode was present, and a conductive paste (manufactured by Fujikura Kasei Co., Ltd.) was applied to the aforementioned portion, followed by drying the solvent from the paste. Using this portion, a voltage was applied to the silicon substrate serving as a gate electrode.

The FET (field-effect transistor) element obtained in this manner was evaluated in terms of its electric properties under the atmospheric air by means of a semiconductor parameter analyzer 4156C manufactured by Agilent Technologies. As a result, the FET element showed properties of a p-type transistor element.

Note that, the following formula was used for calculating the field-effect mobility of the organic thin film transistor.

$$Ids=\mu C_{in}W(Vg-Vth)^2/2L$$

In the formula above, Cin is a capacitance per unit area of the gate insulating film, W is a channel width, L is a cannel length, Vg is a gate voltage, Ids is a source-drain current, μ is mobility, and Vth is threhold voltage at which a channel starts to be formed.

As a result of evaluating the properties of the prepared organic thin film transistor, it was found that the organic thin film transistor had excellent properties such as the field-effect mobility of 1.0 cm$^2$/Vs, threshold voltage of –17V, and on-off ratio of 3.2×10$^7$.

Figure 6:
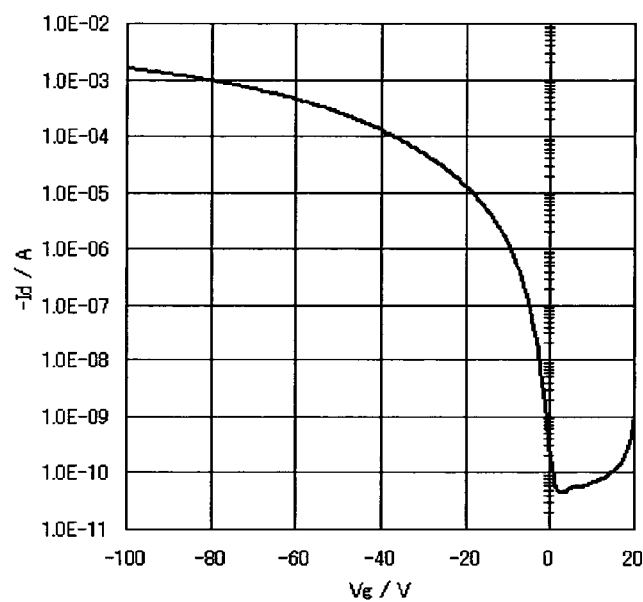
FIG. 6 is a graph showing transferring properties of the organic thin film transistor obtained in Example 4 at Vds=−100V.

The transfer properties of the obtained transistor at Vds=–100V is shown in FIG. 6.

Figure 7:
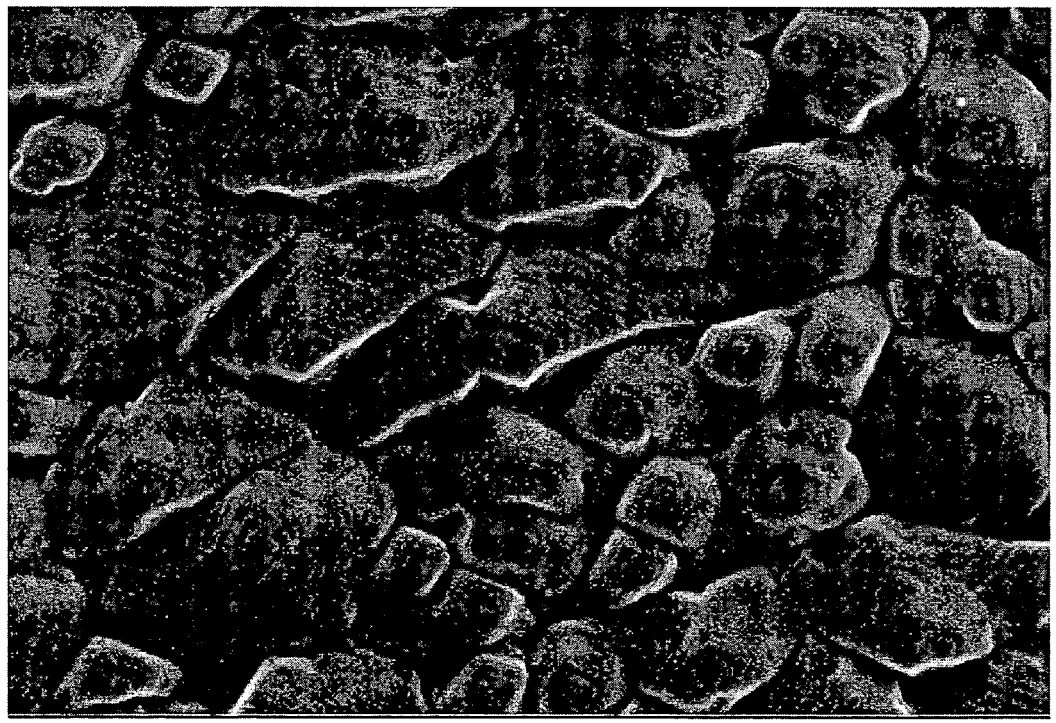
FIG. 7 shows a result of the SEM analysis on the organic thin film transistor prepared in Example 4.

Moreover, as a result of analyzing the obtained transistor under SEM, it was found that the thin film of Compound E1 had a film structure which was tightly grown in the two dimensional planar direction. The result of the SEM analysis is shown in FIG. 7.

Example 5

<Synthesis of Compound E5>

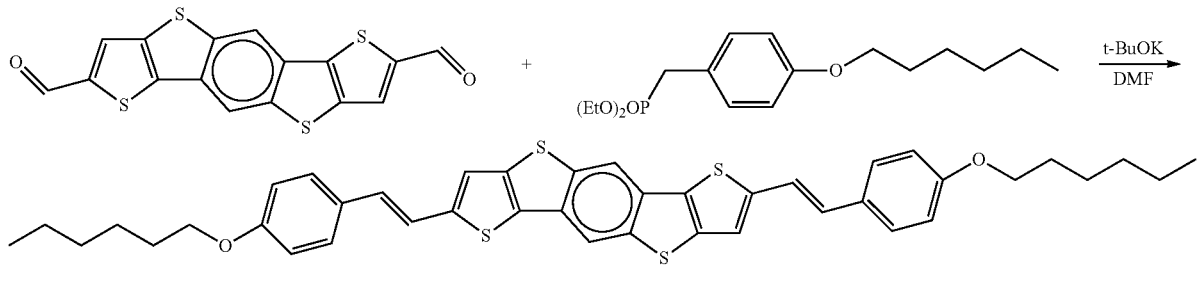

Compound E5

Figure 8:
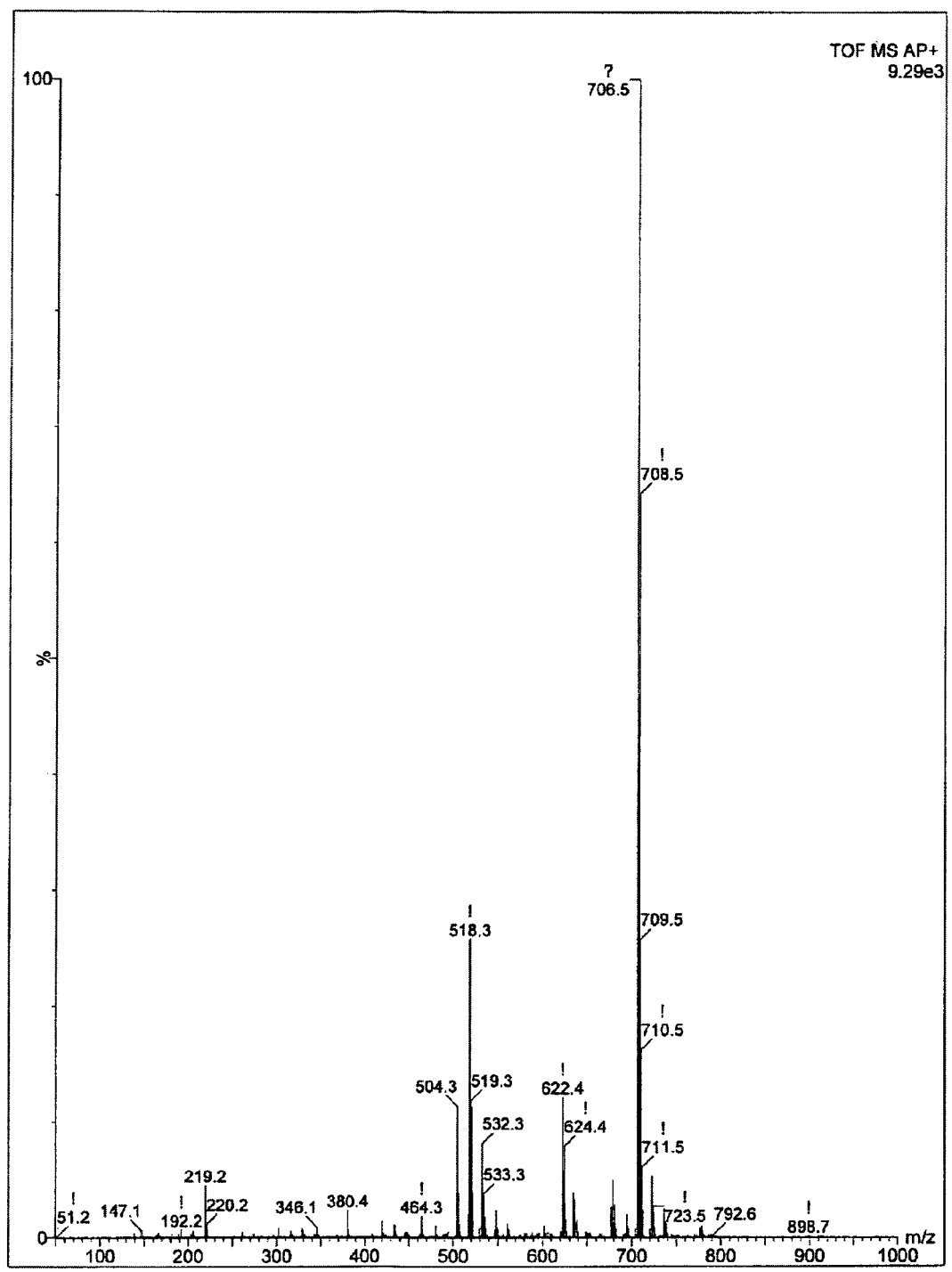
FIG. 8 shows a mass spectrum of Compound E5 synthesized in Example 5.

Compound E5 was obtained in the same manner as in Example 2, provided that 4-decyloxydiethylbenzyl phosphonate was replaced with 4-hexyloxydiethylbenzyl phosphonate. The yield of Compound E5 was 60%. The mass spectrum thereof is shown in FIG. 8.

Example 6

<Synthesis of Compound E6>

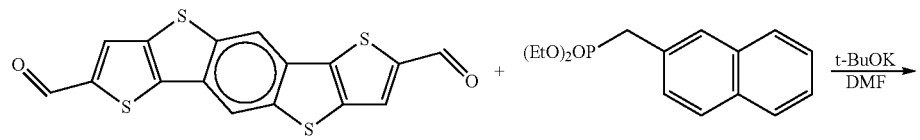

-continued

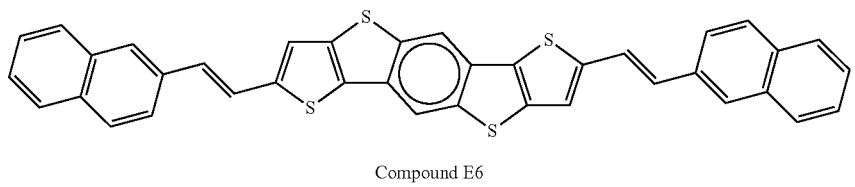

Compound E6

Compound E6 was obtained in the same manner as in Example 2, provided that the above-presented phosphonate synthesized by Michaelis-Arbuzov reaction using 2-(bromomethyl)naphthalene (manufactured by Sigma-Aldrich, Inc.) and triethylphosphite was used. The yield of Compound E6 was 94%.

Moreover, the obtained Compound E6 was subjected to sublimation purification under the reduced pressure of 1E-5 Torr to thereby obtain orange crystals. The purified Compound E5 had a melting point of 386° C., thermal decomposition temperature of 449° C., and ionization potential of 5.3 eV.

IR (KBr): 945 cm$^{-1}$(—CH═CH— trans).

Figure 9:
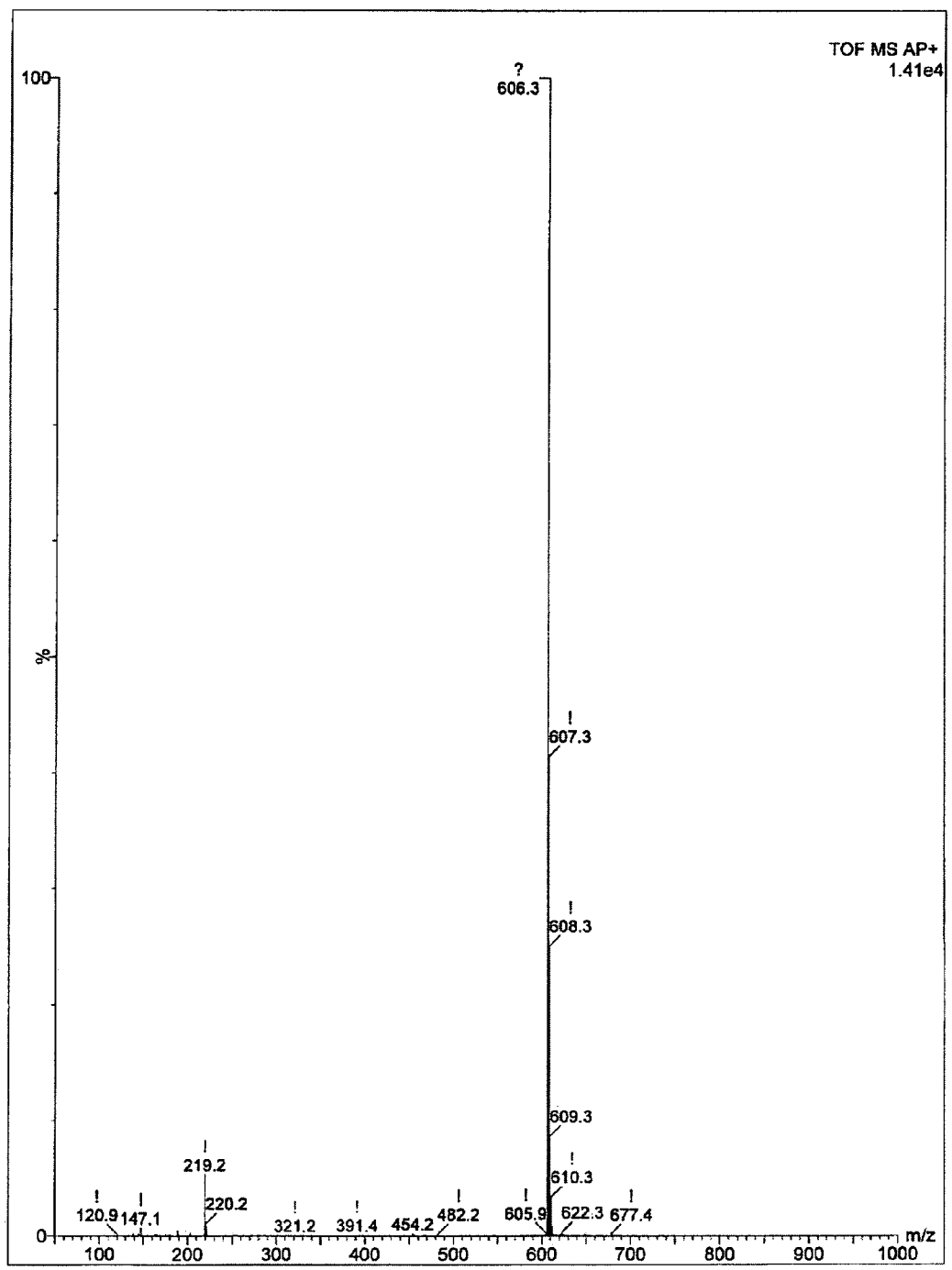
FIG. 9 shows a mass spectrum of Compound E6 synthesized in Example 6.

The mass spectrum of Compound E6 is shown in FIG. 9.

E6 was respectively changed to 180° C., 160° C., 150° C., and room temperature. As a result of the evaluations of the properties of the obtained thin film transistors, they had excellent properties, such as the organic thin film transistors (obtained with the substrate temperature of 180° C., 160° C., 150° C. and room temperature during the deposition) respectively had the field-effect mobility of 2.5E-2 cm$^2$/Vs, 0.3 cm$^2$/Vs to 0.1 cm$^2$/Vs, 0.05 cm$^2$/Vs to 0.03 cm$^2$/Vs, and 2.3E-4 cm$^2$/Vs.

Example 8

<Synthesis of Compound E8>

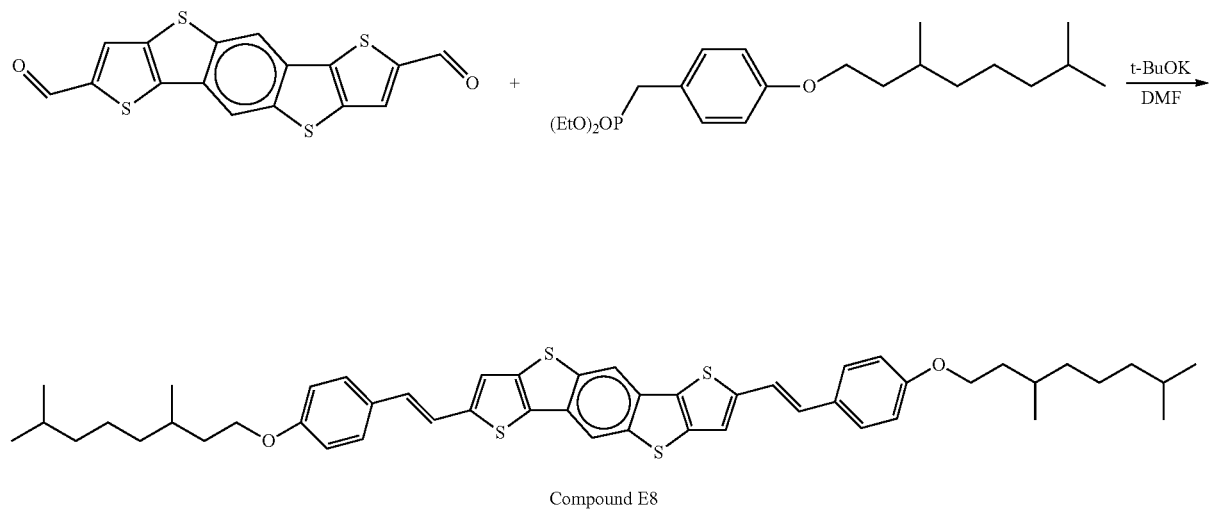

Compound E8

Example 7

Figure 10:
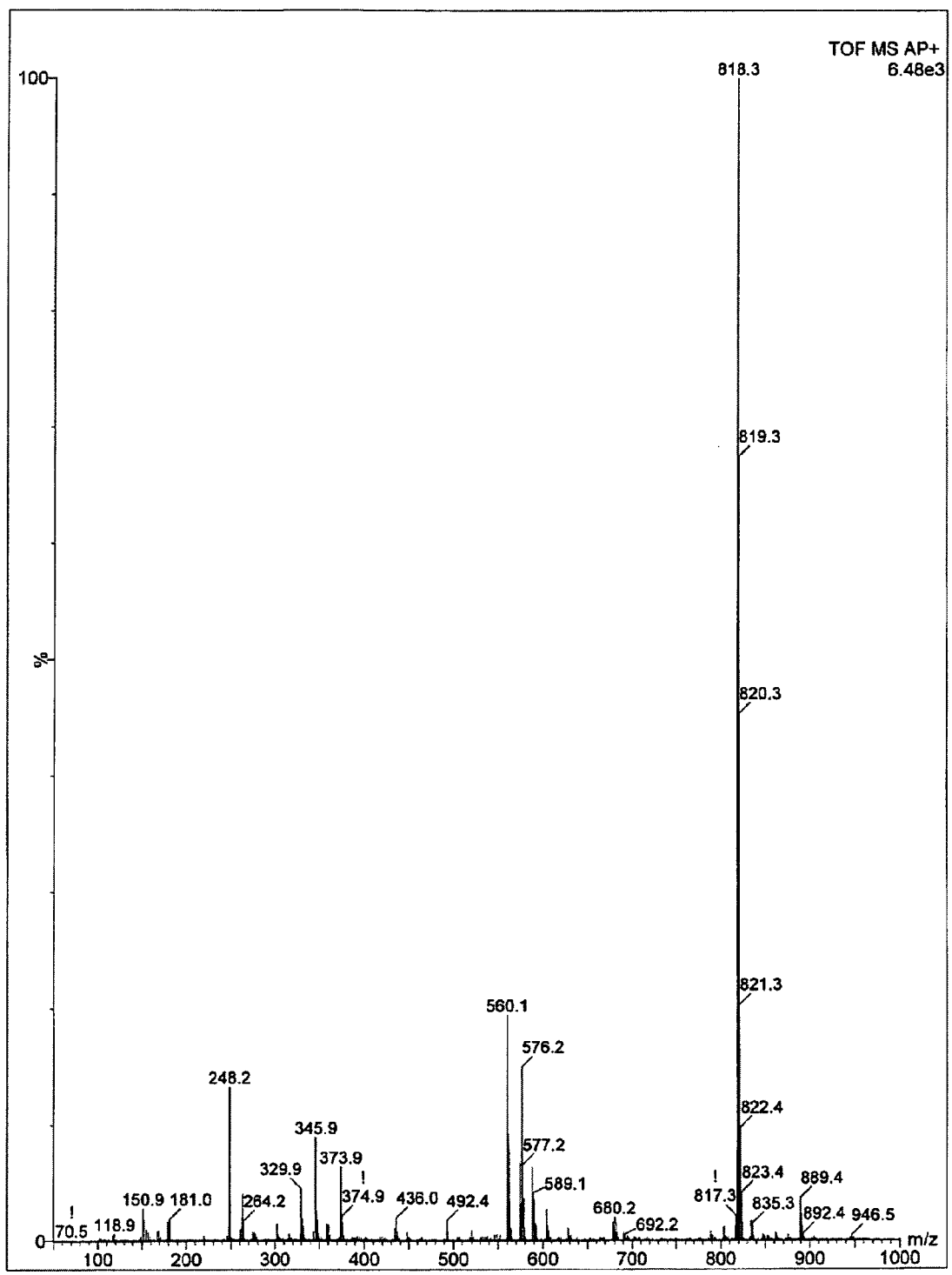
FIG. 10 shows a mass spectrum of Compound E8 synthesized in Example 8.

Organic thin film transistors of Compound E6 were obtained in the same manner as in Example 4, provided that the substrate temperature during the deposition of Compound Compound E8 was obtained in the same manner as Example 2, provided that 4-decyloxydiethylbenzyl phosphonate was replaced with 4-(3,7-dimethyloctyloxy)diethylbenzyl phosphonate. The yield of Compound E8 was 68%. The mass spectrum of Compound E8 is shown in FIG. 10.

Example 9

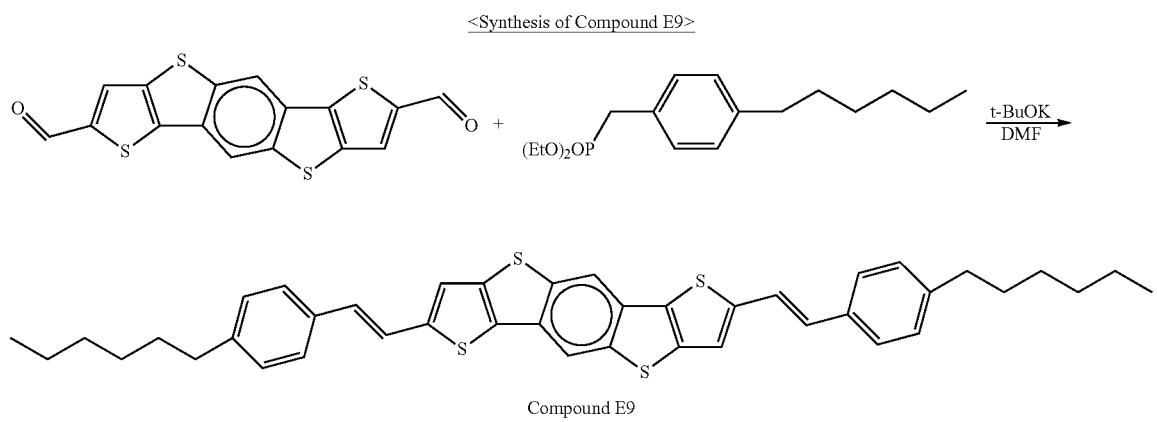

Compound E9

Figure 11:
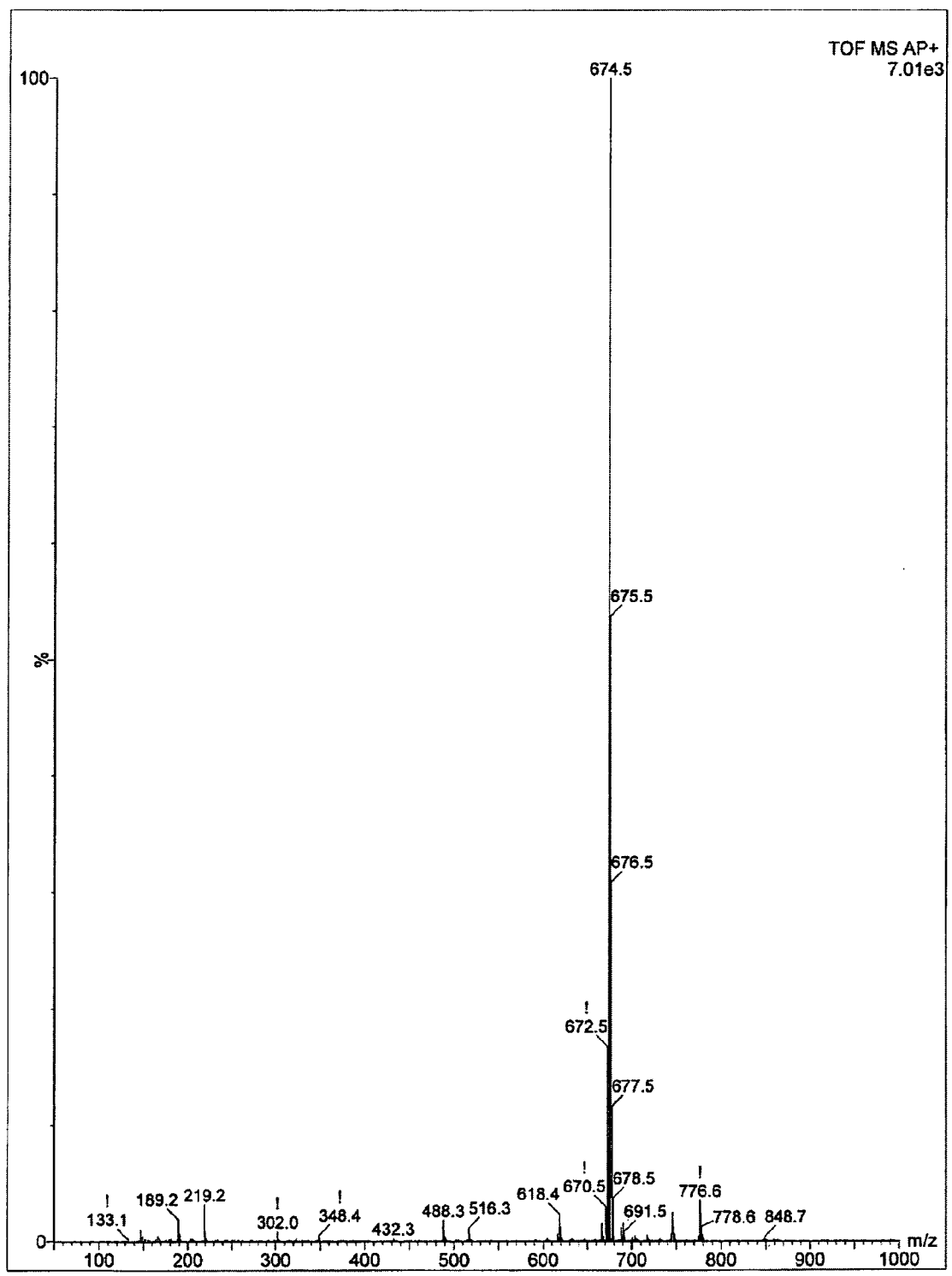
FIG. 11 shows a mass spectrum of Compound E9 synthesized in Example 9.

Compound E9 was obtained in the same manner as Example 2, provided that 4-decyloxydiethylbenzyl phosphonate was replaced with 4-hexyldiethylbenzyl phosphonate. The yield of Compound E9 was 68%. The mass spectrum of Compound E9 is shown in FIG. 11.

Example 10

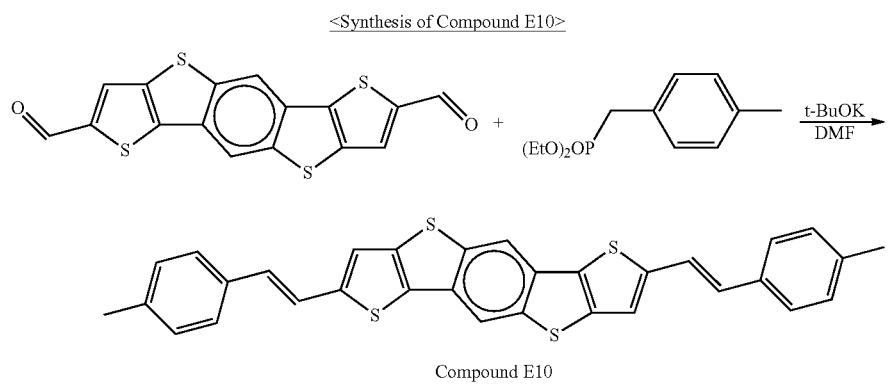

Compound E10

Figure 12:
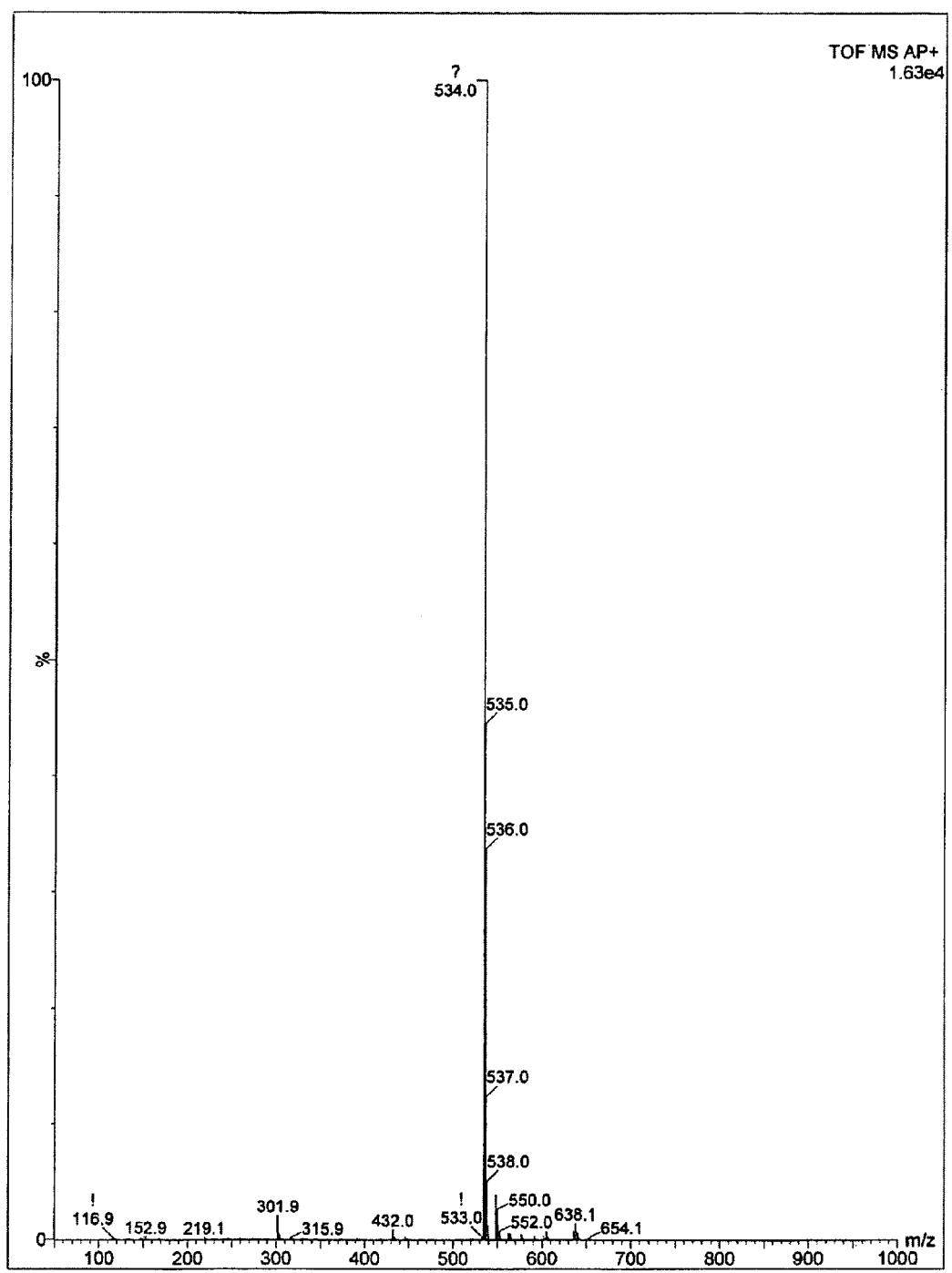
FIG. 12 shows a mass spectrum of Compound E10 synthesized in Example 10.

Compound E10 was obtained in the same manner as Example 2, provided that 4-decyloxydiethylbenzyl phosphonate was replaced with 4-methyldiethylbenzyl phosphonate. The yield of Compound E10 was 92%. In addition, the obtained Compound E10 was subjected to sublimation purification under the reduced pressure of 1E-5 Torr to thereby obtain orange crystals. The purified Compound E10 had a melting point of 369° C., thermal decomposition temperature of 423° C., and ionization potential of 5.2 eV. The mass spectrum of Compound E10 is shown in FIG. 12.

Example 11

Organic thin film transistors of Compound E10 were obtained in the same manner as in Example 4, provided that the substrate temperature during the deposition of Compound E10 was respectively changed to 180° C., 150° C., 100° C., and room temperature.

As a result of the evaluation on the obtained organic thin film transistors, the organic thin film transistors (obtained with the substrate temperature of 180° C., 150° C., 100° C., and room temperature, respectively) had excellent properties, such as the field-effect mobility of 2.5 cm²/Vs to 1.7 cm²/Vs, 2.3 cm²/Vs to 1.9 cm²/Vs, 1.5 cm²/Vs to 1.4 cm²/Vs, and 0.2 cm²/Vs to 0.3 cm²/Vs, respectively.

Figure 13:
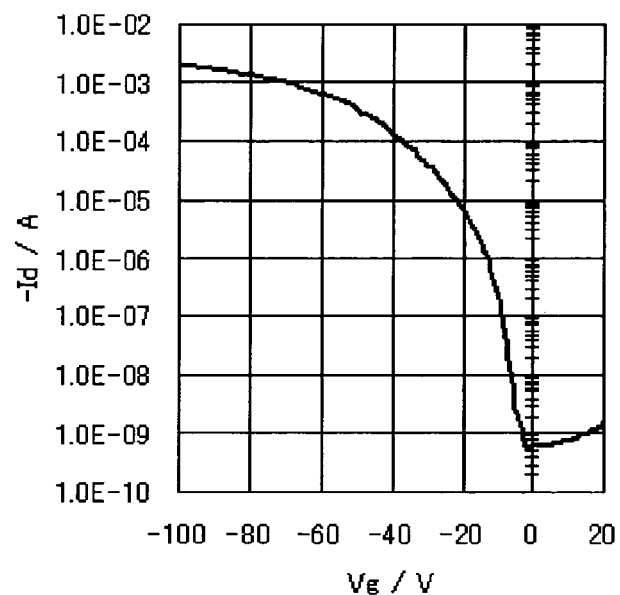
FIG. 13 shows transfer properties of the transistor obtained in Example 11 at Vds=−100V.

The transfer property of the organic thin film transistor (which was obtained with the substrate temperature of 180° C. during the deposition) at Vds=−100V is shown in FIG. 13.

Figure 14:
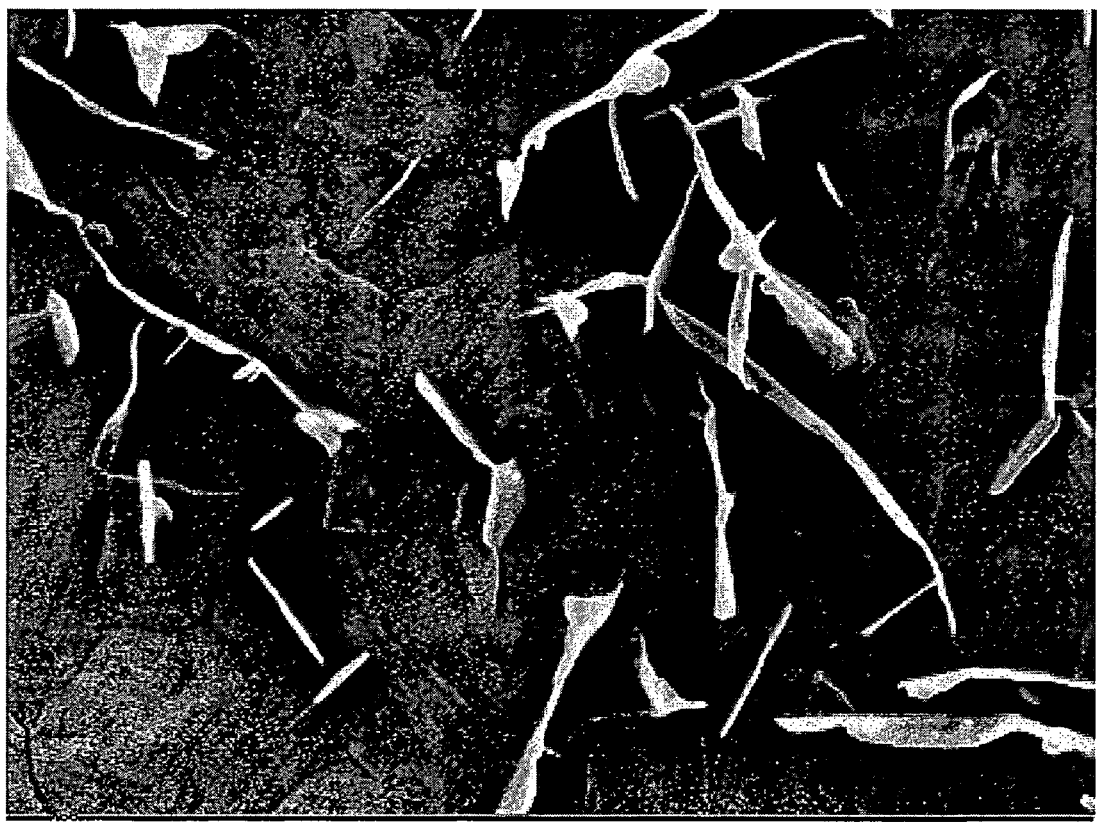
FIG. 14 is a SEM image of the transistor obtained in Example 11.

Moreover, the obtained organic thin film transistor was analyzed under SEM, and it was found that the thin film of Compound E10 had a film structure which was tightly grown in the two dimensional planar direction. The result of the SEM analysis is shown in FIG. 14.

Example 12

<Synthesis of Compound E12>

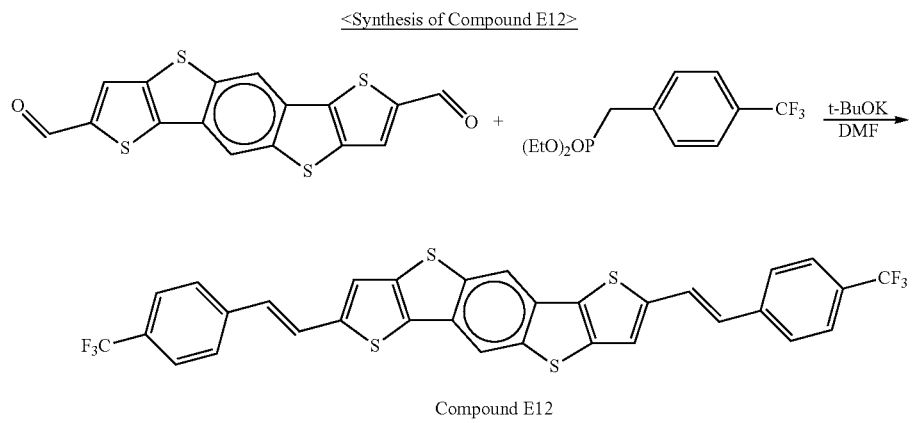

Compound E12

Compound E12 was obtained in the same manner as in Example 2, provided that 4-decyloxydiethylbenzyl phosphonate was replaced with 4-trifluoromethyldiethylbenzyl phosphonate. The yield of Compound E12 was 88%. Moreover, the obtained Compound E12 was subjected to sublimation purification under the reduced pressure of 1E-5 Torr to thereby obtain yellow crystals. The purified Compound E12 had a melting point of 370° C., thermal decomposition temperature of 386° C. and ionization potential of 6.1 eV.

Figure 15:
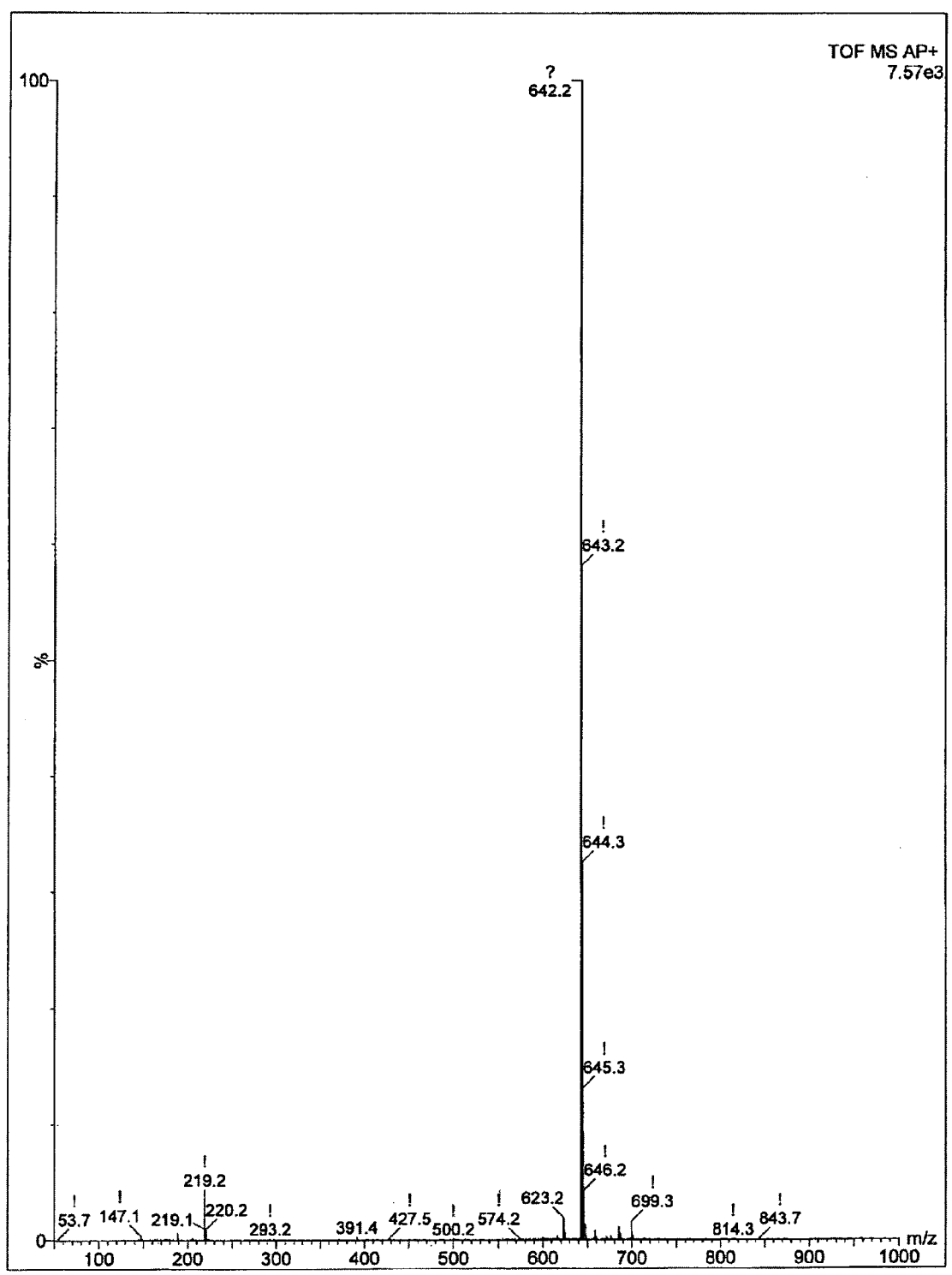
FIG. 15 shows a mass spectrum of Compound E12 synthesized in Example 12.

The mass spectrum of Compound E12 is shown in FIG. 15.

An organic thin film transistor of Compound E12 was obtained in the same manner as in Example 4, provided that the substrate temperature during the deposition of Compound E12 was respectively changed to 140° C., and the materials for the source electrode and drain electrode were both changed to Ca.

As a result of the evaluation on the obtained organic thin film transistor in a glove box, the organic thin film transistor showed characteristics of a n-type transistor element, and had excellent properties such as the field-effect mobility of 0.2 $cm^2/Vs$.

Figure 16:
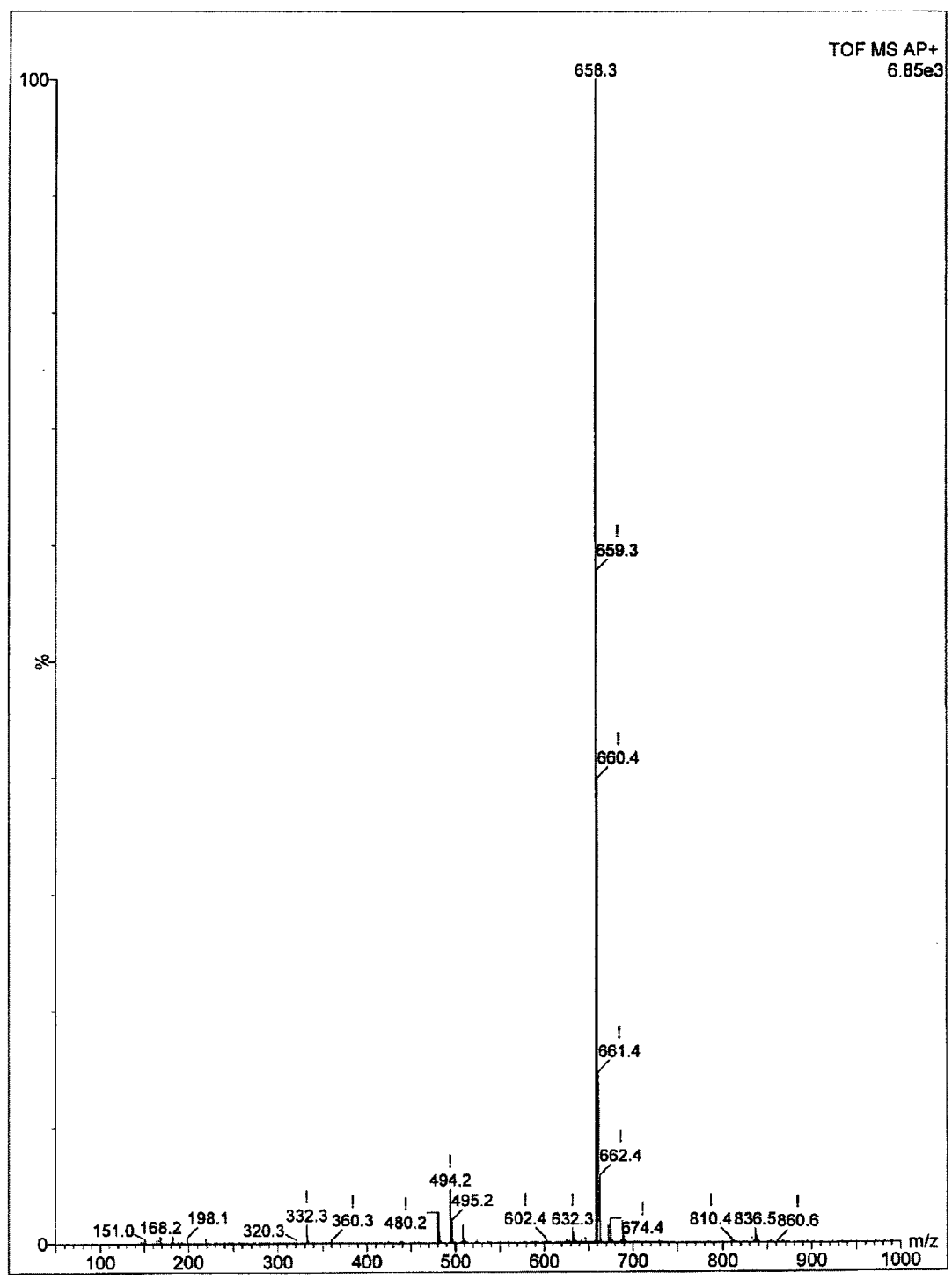
FIG. 16 shows a mass spectrum of Compound E13 synthesized in Example 13.

Compound E13 was obtained in the same manner as in Example 2, provided that 4-decyloxydiethylbenzyl phosphonate was replaced with 4-phenyldiethylbenzyl phosphonate. The yield of Compound E13 was 95%. The purified Compound E13 had a melting point of 434° C., thermal decomposition temperature of 450° C. or lower and ionization potential of 5.2 eV. The mass spectrum of Compound E13 is shown in FIG. 16.

An organic thin film transistor of Compound E13 was obtained in the same manner as in Example 4, provided that the substrate temperature during the deposition of Compound E13 was respectively changed to 200° C.

As a result of the evaluation on the obtained organic thin film transistor, the organic thin film transistor showed characteristics of a p-type transistor element, and had excellent properties such as the field-effect mobility of 0.20 $cm^2/Vs$ to 0.43 $cm^2/Vs$, and on-off ratio of $10^7$.

Example 13

<Synthesis of Compound E13>

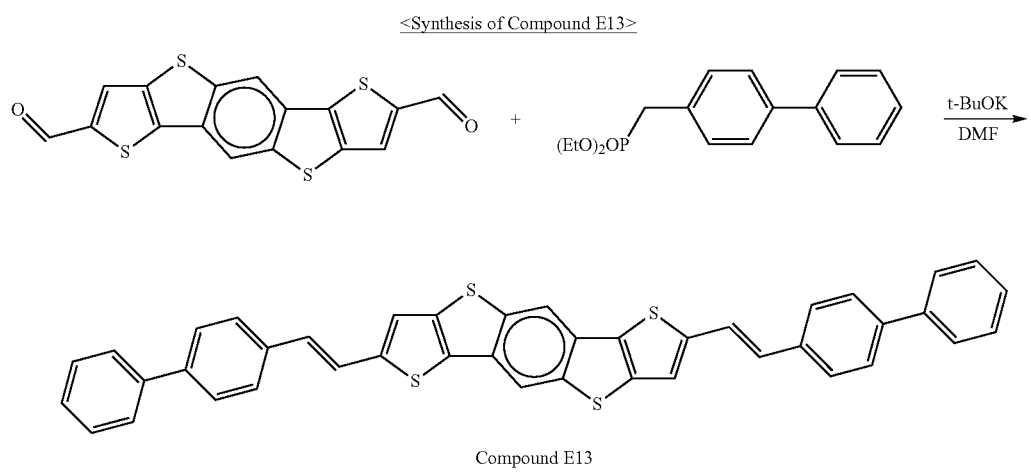

Compound E13

Example 14

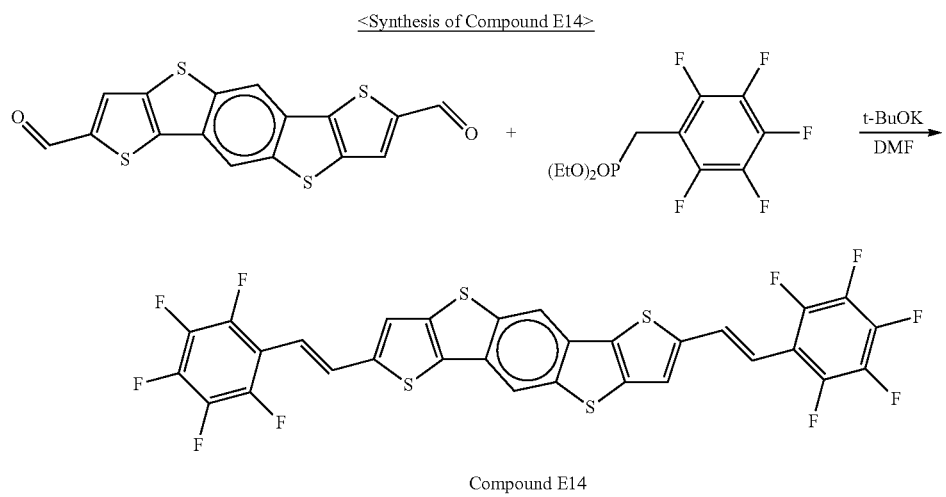

Compound E14

Compound E14 was obtained in the same manner as in Example 2, provided that the above-presented phosphonate synthesized by Michaelis-Arbuzov reaction using 2,3,4,5,6-pentafluorobenzyl bromide (manufactured by Sigma-Aldrich, Inc.) and triethylphosphite was used. The yield of Compound E14 was 74%.

Figure 17:
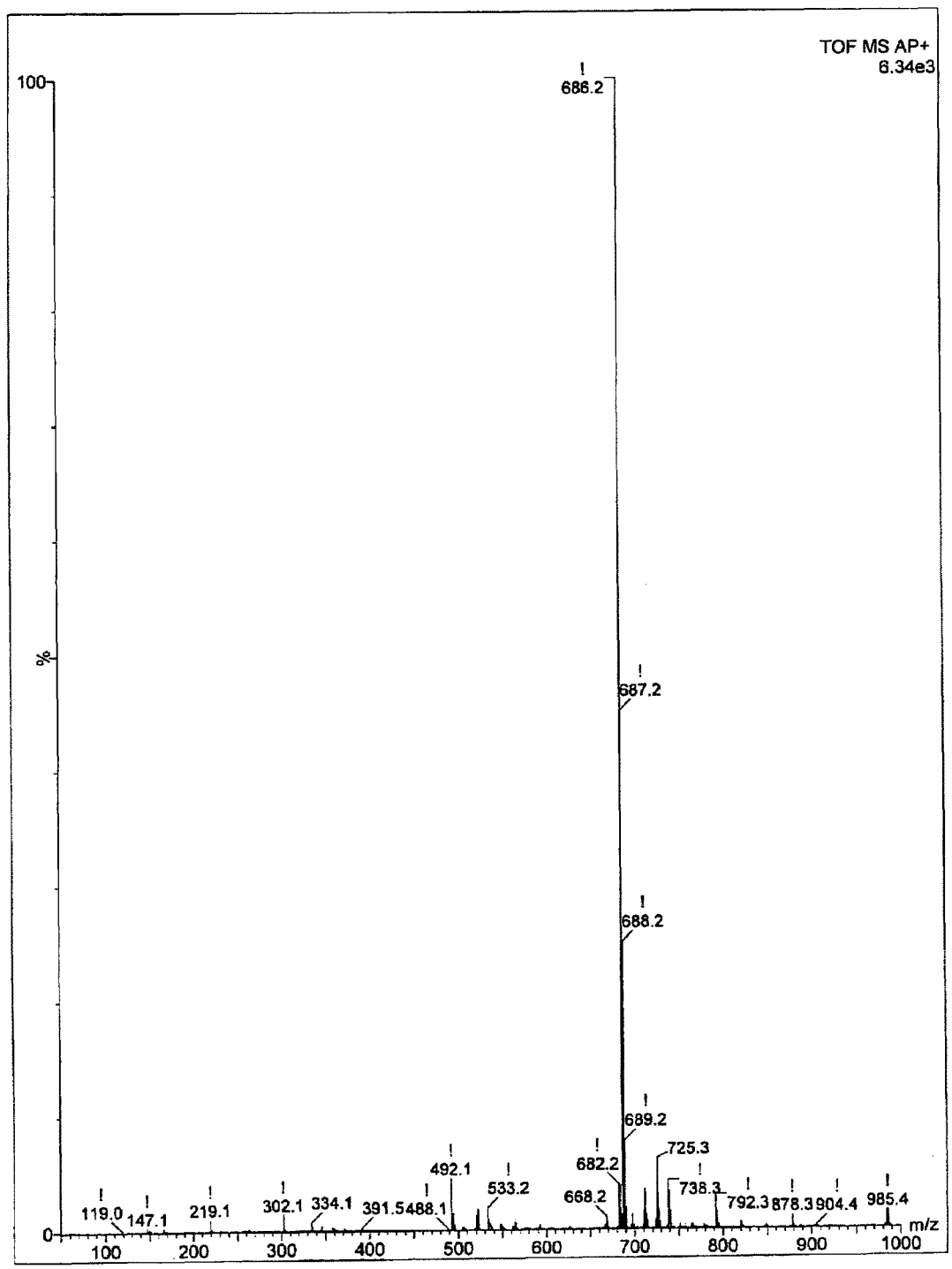
FIG. 17 shows a mass spectrum of Compound E14 synthesized in Example 14.

The mass spectrum of Compound E14 is shown in FIG. 17.

Example 15

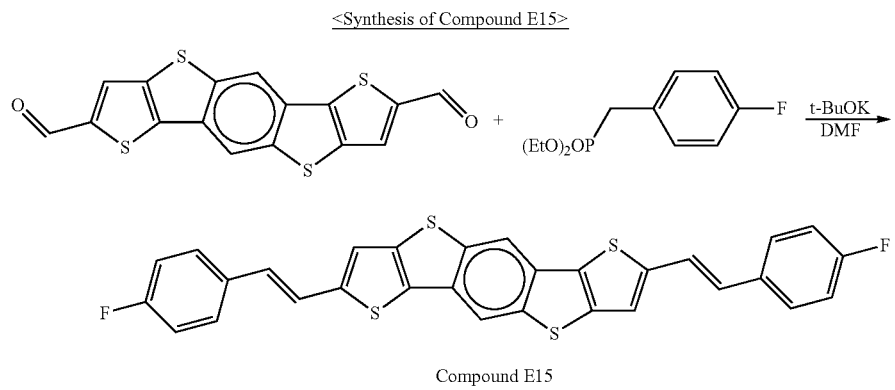

Compound E15

Compound E 15 was obtained in the same manner as in Example 2, provided that the above-presented phosphonate synthesized by Michaelis-Arbuzov reaction using 4-fluorobenzyl chloride (manufactured by Tokyo Chemical Industry Co., Ltd.) and triethyl phosphate was used. The yield of Compound E15 was 67%. The obtained Compound E15 was purified by recrystallization of o-dichlorobenzene, to thereby obtain yellow crystals. The purified Compound E15 had a melting point of 353° C., thermal decomposition temperature of 410° C. and ionization potential of 5.6 eV.

Figure 18:
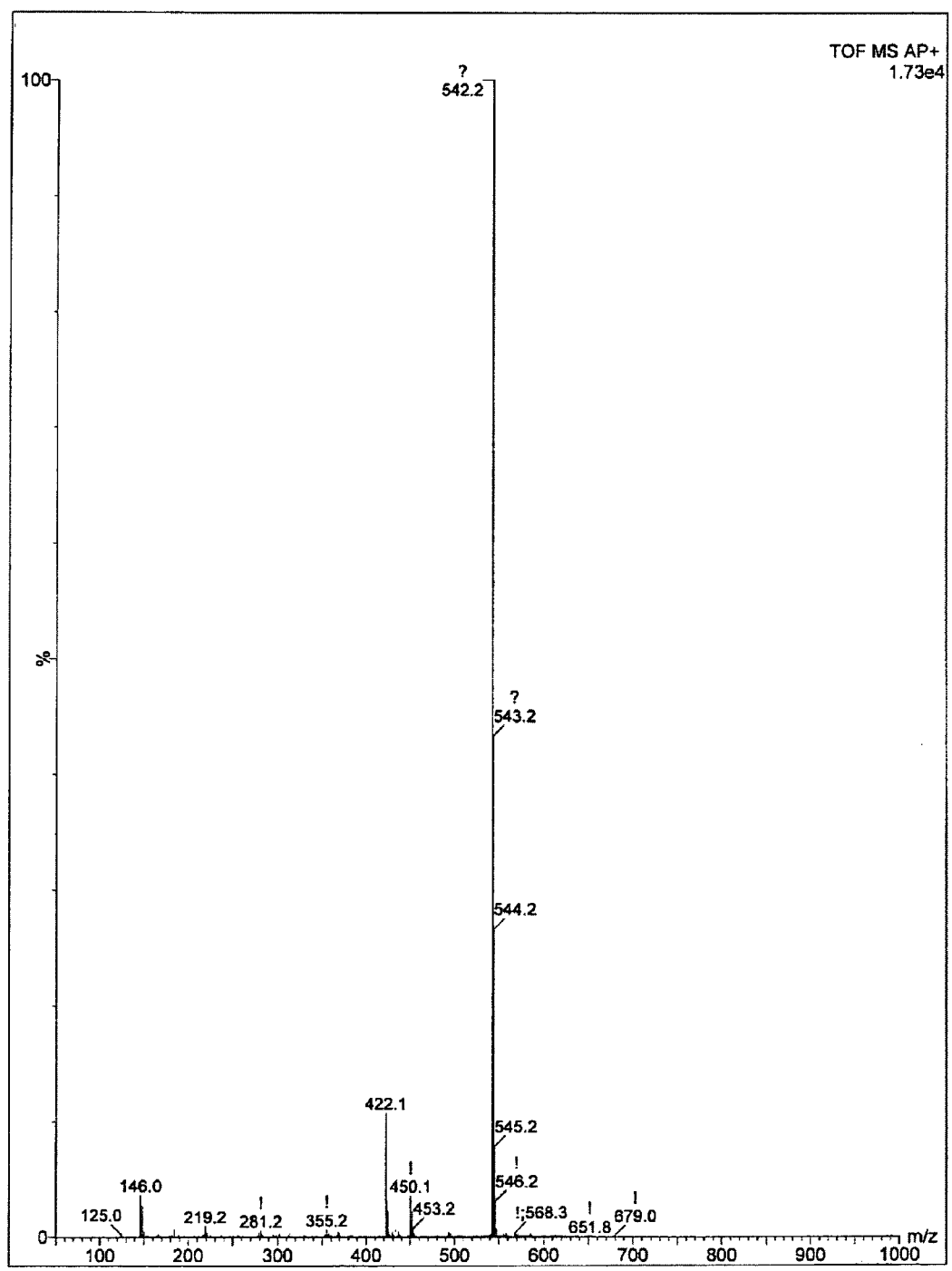
FIG. 18 shows a mass spectrum of Compound E15 synthesized in Example 15.

The mass spectrum of Compound E15 is shown in FIG. 18.

Example 16

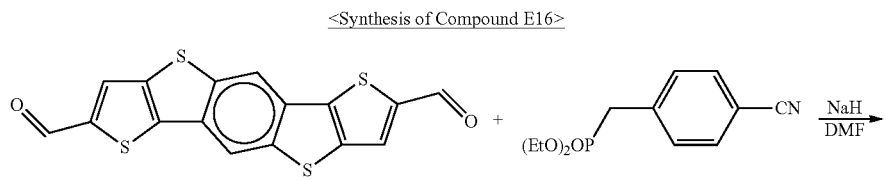

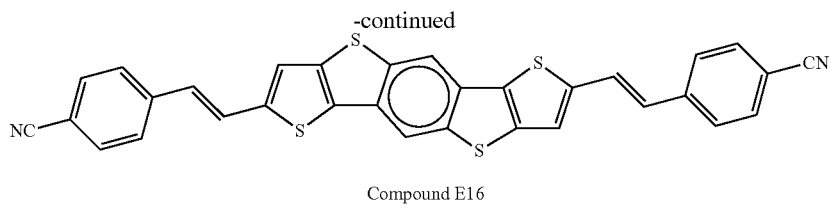

Compound E16

Into a 1L flask, 1.987 g (7.811 mmol) of 4-cyanodiethylbenzyl phosphonate, and 0.700 g (1.953 mmol) of dialdehyde (Compound S7) (which had been crushed by a mortar) were added. The inner atmosphere of the flask was then replaced with argon gas, and 500 mL of dehydrated DMF was added thereto. Thereafter, the mixture was dispersed by ultrasonic radiation. After adding 0.340 g (7.811 mmol) of NaH (55% in liquid paraffin) to the mixed solution, the solution was stirred at 60° C. for 1.5 hours. The obtained reaction solution was cooled to room temperature, and a small amount of acetic acid was added thereto. After removing approximately 400 mL of the solvent from the solution under reduced pressure, water was added thereto. The precipitated solids in the solution were then removed by filtration, followed by washing with methanol, acetone, and hexane, respectively. The washed solids were then vacuum-dried to thereby obtain 1.025 g of Compound E 16. The yield of Compound E16 was 94%.

Figure 19:
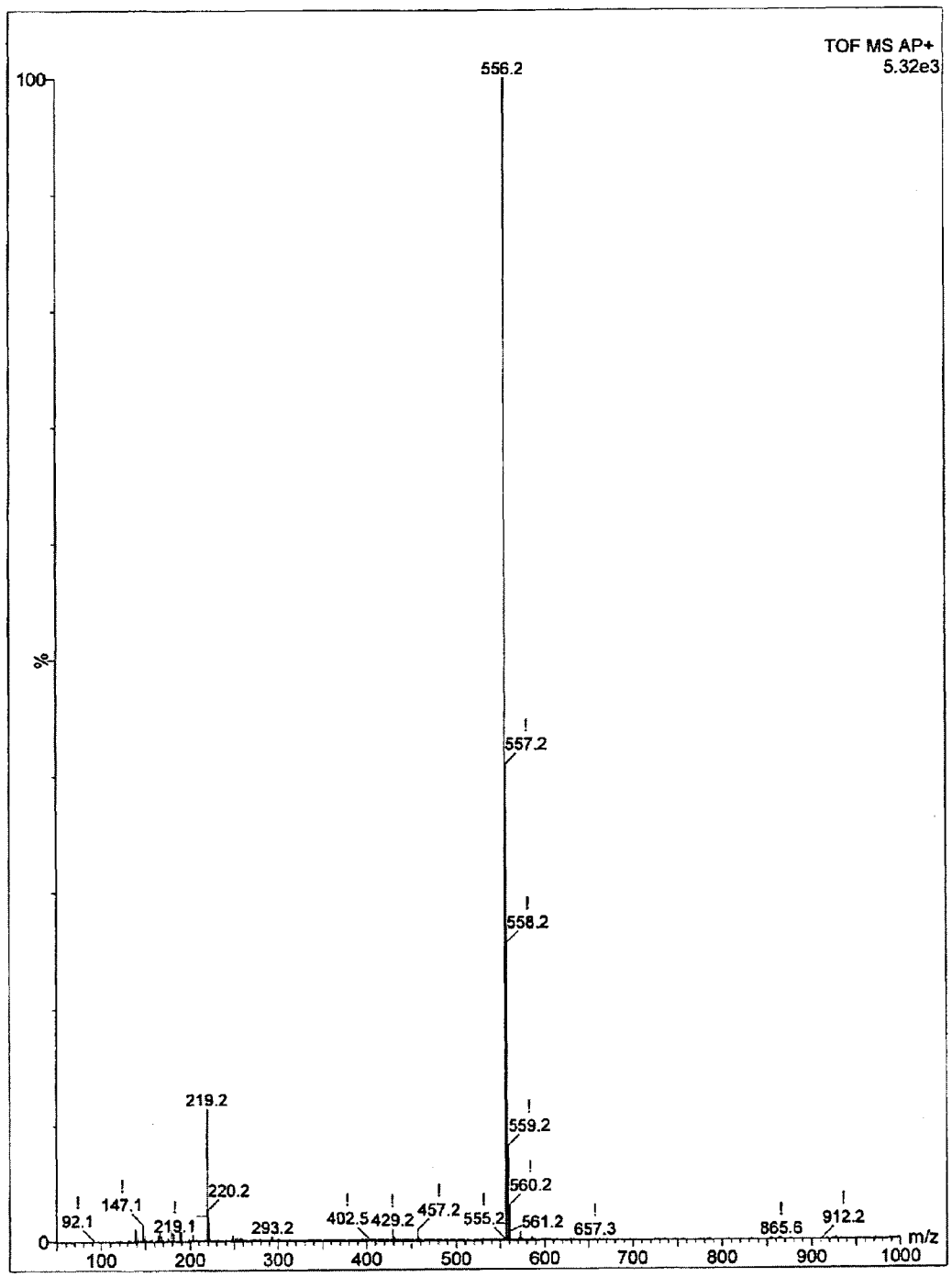
FIG. 19 shows a mass spectrum of Compound E16 synthesized in Example 16.

The mass spectrum of Compound E16 is shown in FIG. 19.

Example 17

<Synthesis of Compound E17>

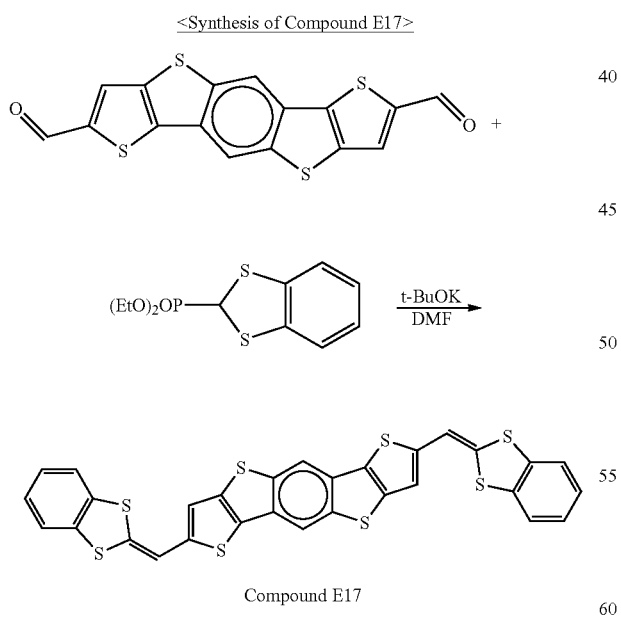

Compound E17

Figure 20:
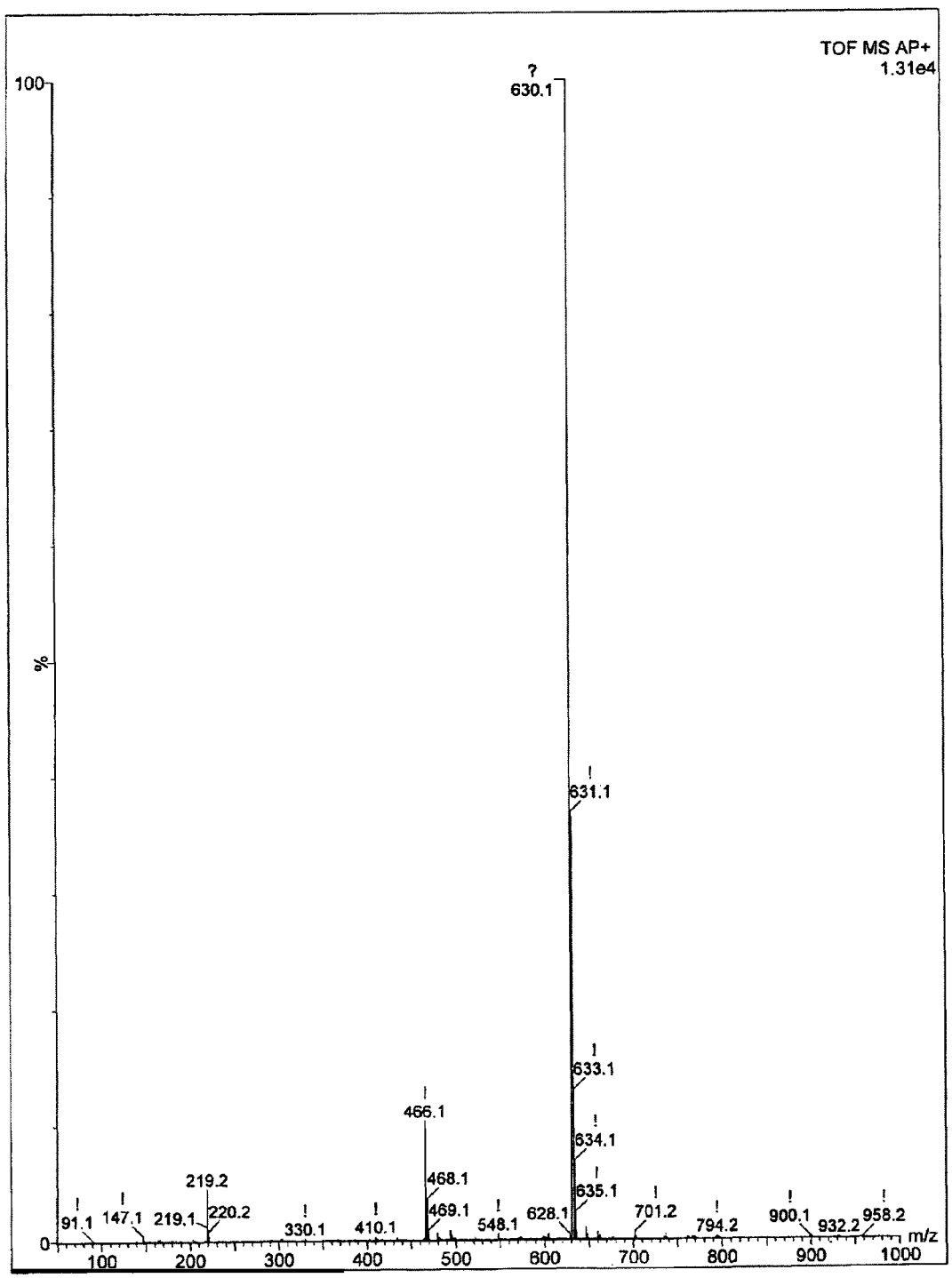
FIG. 20 shows a mass spectrum of Compound E17 synthesized in Example 17.

Compound E17 was obtained in the same manner as in Example 2, provided that 4-decyloxydiethylbenzyl phosphonate was replaced with the above-presented phosphonate. The yield of Compound E17 was 92%. The mass spectrum of Compound E17 is shown in FIG. 20.

Example 18

<Synthesis of Compound E18>

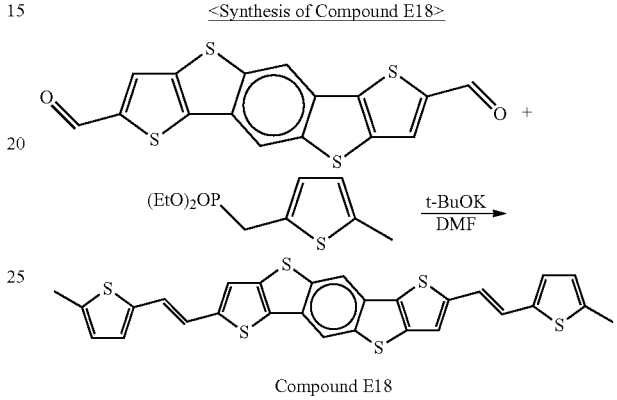

Compound E18

Figure 21:
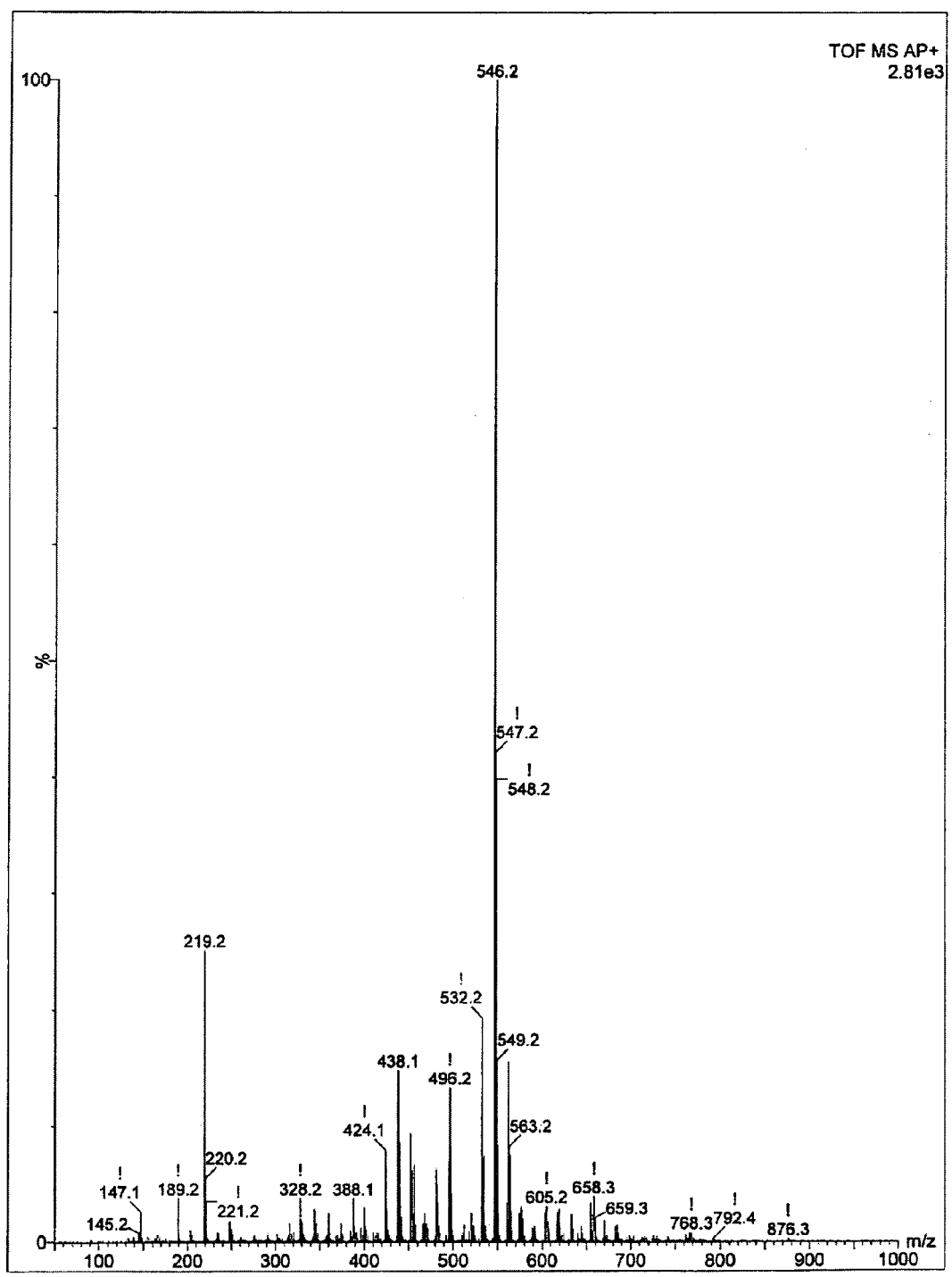
FIG. 21 shows a mass spectrum of Compound E18 synthesized in Example 18.

Compound E18 was obtained in the same manner as in Example 2, provided that 4-decyloxydiethylbenzyl phosphonate was replaced with the above-presented phosphonate. The yield of Compound E18 was 75%. The mass spectrum of Compound E18 is shown in FIG. 21.

Comparative Example 1

Compound S6 (which had been used as a starting material in Example 2) was dissolved in THF, and this solution was applied onto a silicon wafer by cast-coating to form a film thereon.

Compound S6 was precipitated as needle crystals as the solvent dried. Therefore, a continuous film, which would be usable as a charge transporting member, could not be obtained. Moreover, monocrystals of Compound S6 were obtained from the THF solution, and were subjected to X-ray analysis for the crystal structure. As a result, it was found that the monocrystals had a structure in which molecules were stacked by π-π interaction.

Comparative Example 2

An organic thin film transistor was obtained in the same manner as in Example 5, provided that Compound S6 was used. The properties of the obtained organic thin film transistor were evaluated, but the organic thin film transistor did not work as a transistor.

The obtained organic thin film transistor was observed under SEM, and it was found that needle crystals were grown.

Accordingly, similarly to the case of Comparative Example 1, a continuous film which would be usable as a charge transporting member could not be obtained.

Figure 22:
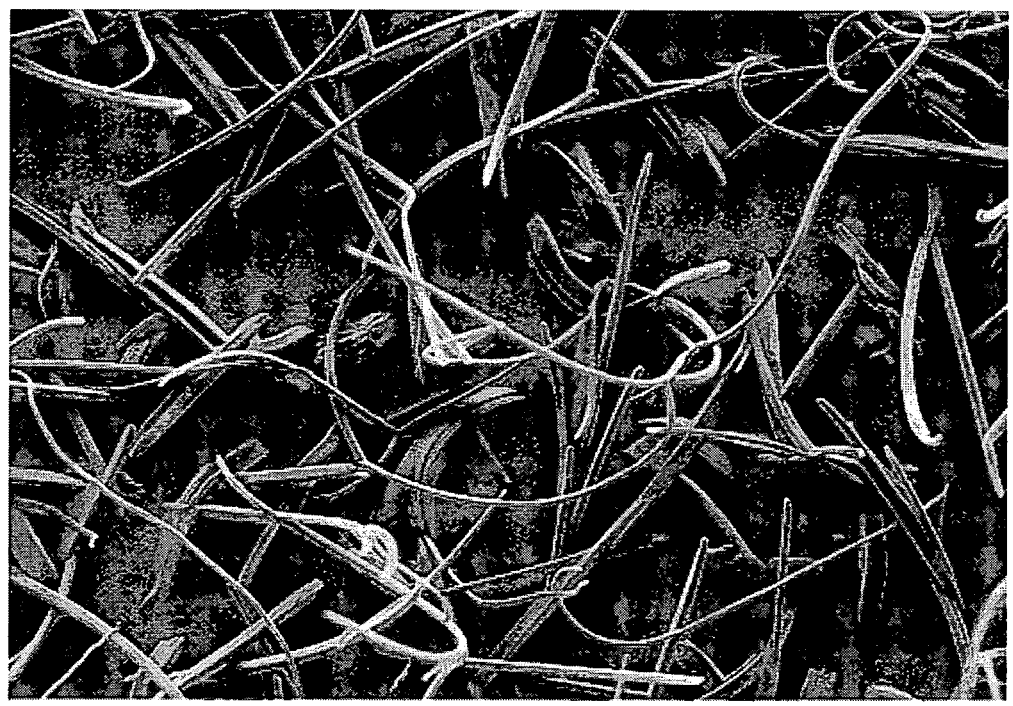
FIG. 22 is a SEM image of the transistor obtained in Comparative Example 2.

The results of the SEM analysis are shown in FIG. 22.

Comparative Example 3

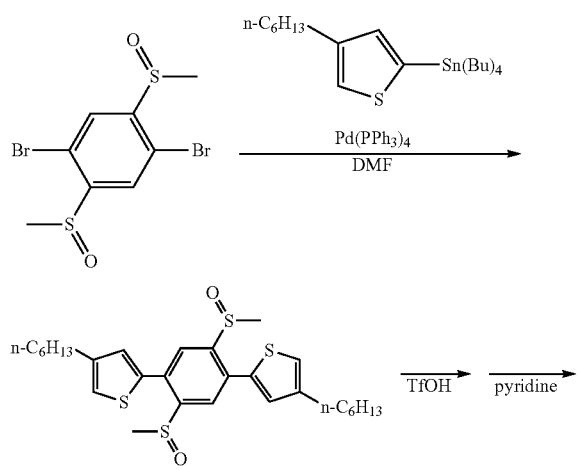

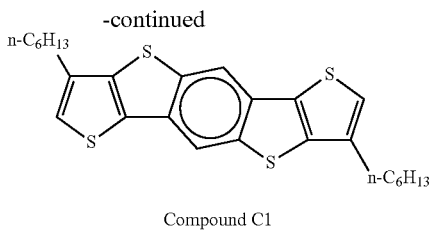
Compound C1

Compound C1 was synthesized through the above-presented reactions, with reference to Advanced Materials, 2009, 21, 213-216 (NPL 4). Compound C1 was in the form of colorless needle crystals, and had a melting point of 184° C. Moreover, monocrystals of Compound C1 were obtained from the THF solution, and were subjected to an X-ray analysis for the crystal structure. As a result, it was found that the monocrystals had a structure in which molecules were stacked by π-π interaction.

Figure 1C:
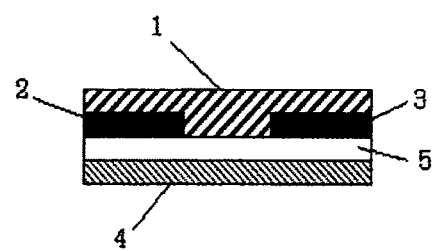
Figure 1B:
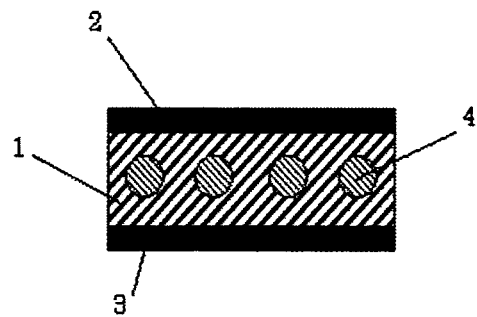
Figure 1D:
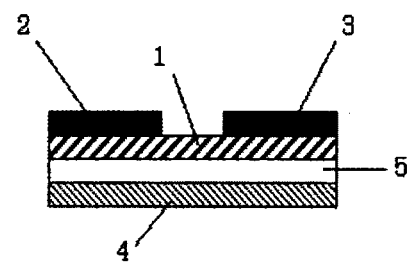

Onto a substrate which had a silicon wafer having a 300 nm-thick thermal oxide film and gold electrodes patterned thereon, a 0.5% by weight methylene solution of Compound C1 was applied by cast-coating to form a film, to thereby obtain an organic thin film transistor having the structure shown in FIG. 1C. The properties of the obtained organic thin film transistor were evaluated, but it did not work as a transistor, and thus it was assumed that an element had the mobility of approximately 1E-5.

Figure 23:
FIG. 23 is a SEM image of the transistor obtained in Comparative Example 3.
Figure 24:
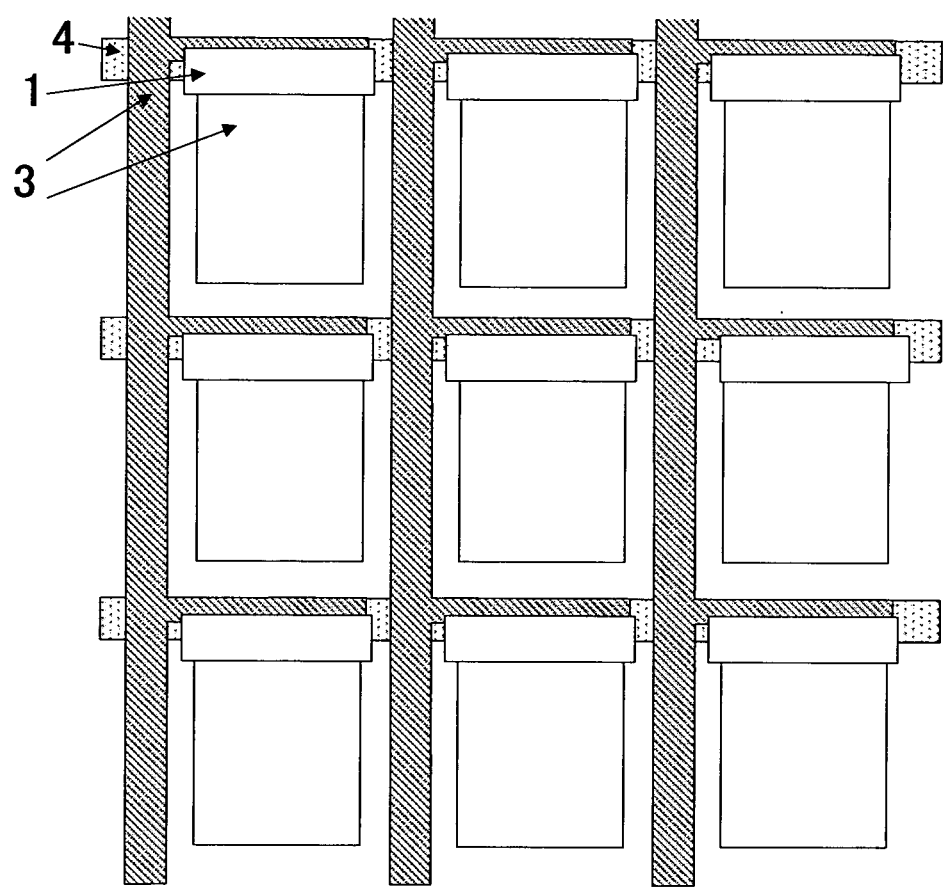
FIG. 24 is a schematic diagram showing one example of a transistor array for driving a display element.
Figure 25:
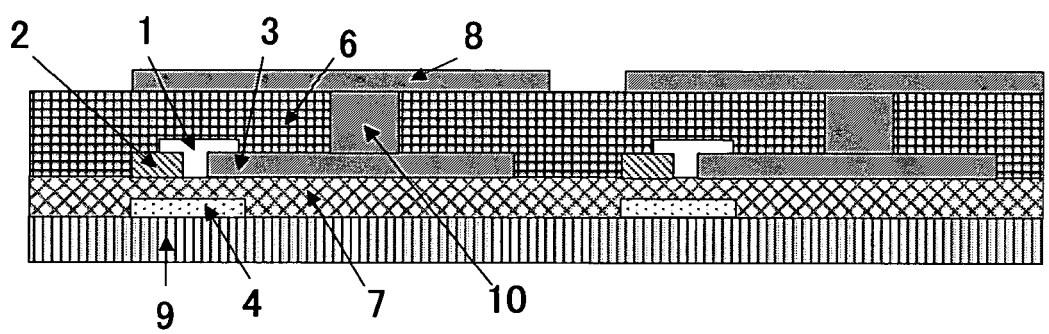
FIG. 25 is a schematic cross-sectional diagram showing one example of a transistor array for driving a display element.

The obtained organic thin film transistor was observed under SEM, and it was found that needle crystals were grown. Accordingly, similarly to the case of Comparative Example 1, a thin continuous film which would be usable as a charge transferring member could not be obtained. The result of the SEM analysis is shown in FIG. 23.

Example 19

<Synthesis of Compound E19>

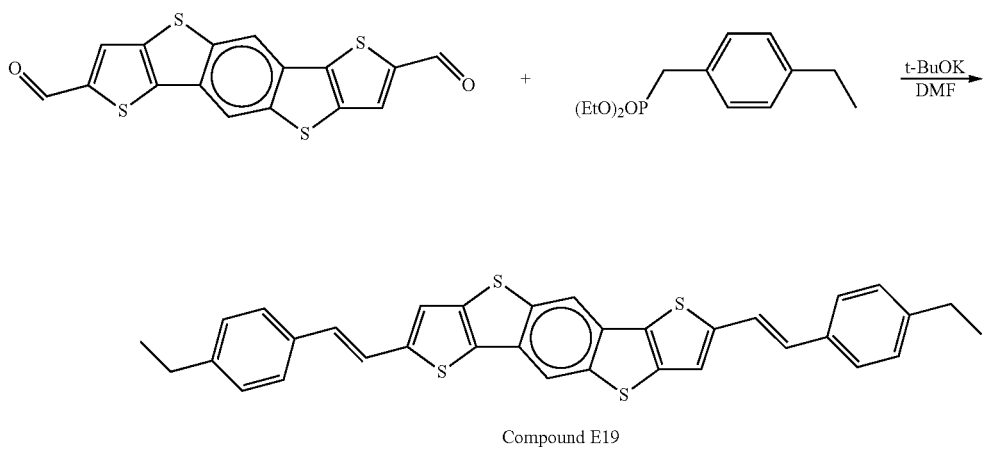

Compound E19

Compound E19 was obtained in the same manner as in Example 2, provided that 4-decyloxydiethylbenzyl phosphonate was replaced with 4-ethyldiethylbenzyl phosphonate. Compound E19 was obtained by recrystallization of o-dichlorobenzene, and the yield of Compound E19 was 79%. The purified Compound E19 had a melting point of 353° C., thermal decomposition temperature of 400° C. and ionization potential of 5.1 eV.

An organic thin film transistor of Compound E19 was obtained in the same manner as in Example 4, provided that the substrate temperature during the deposition of Compound E19 was changed to 170° C. As a result of the evaluation on the obtained organic thin film transistor, the organic thin film transistor showed characteristics of a p-type transistor element, and had excellent properties such as the field-effect mobility of 1.1 cm²/Vs.

Example 20

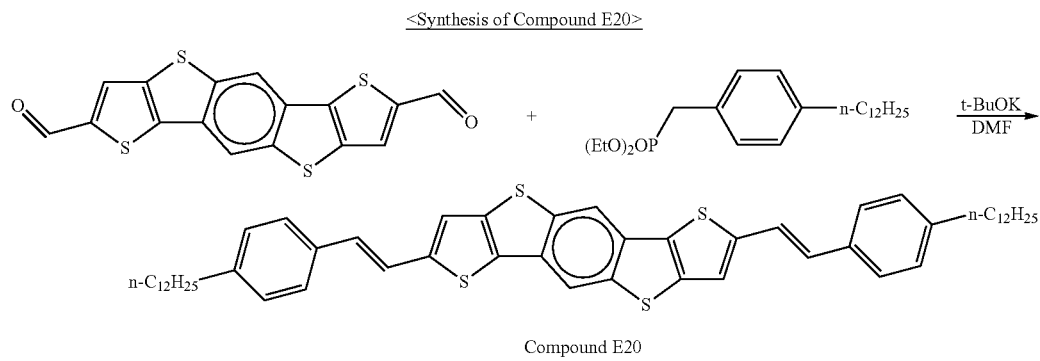

Compound E20 was obtained in the same manner as in Example 2, provided that 4-decyloxydiethylbenzyl phosphonate was replaced with 4-dodecyldiethylbenzyl phosphonate. Compound E20 was obtained by recrystallization of o-dichlorobenzene, and the yield of Compound E20 was 45%. LC-MS: 842.605 (100.0%), 843.608 (58.4%), 844.601 (18.1%), 844.611 (16.7%)

As a result of an analysis conducted on Compound E19 in accordance with DSC, phase transition temperature was observed at 110° C., 165° C., 222° C., and 262° C.

Reference Signs List
1 Organic semiconductive layer
2 First electrode (source electrode)
3 Second electrode (drain electrode)
4 Third electrode (gate electrode), scanning line
5 Insulating film
6 Interlayer insulating film
7 Gate insulating film
8 Pixel electrode
9 Substrate
10 Through-hole

The invention claimed is:

1. A crystalline organic semiconductive material which is a herringbone packing, represented by formula (I):

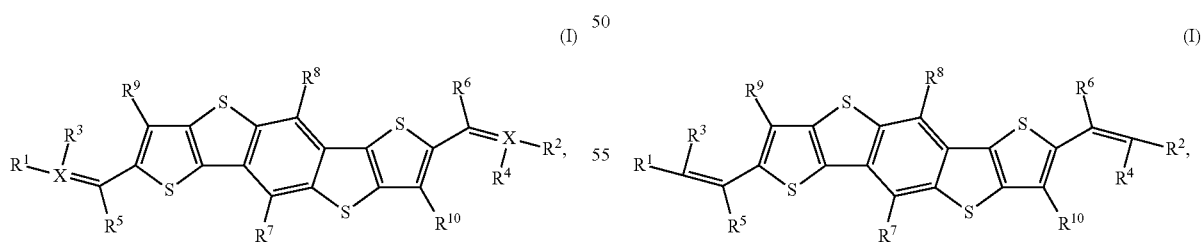

wherein:
R$^1$ to R$^{10}$ independently represent a hydrogen atom, a substituted or unsubstituted alkyl group, a substituted or unsubstituted alkoxy group, a substituted or unsubstituted alkylthio group, or a substituted or unsubstituted aryl group, optionally bonded to each other to form a ring; and X is a carbon atom or a nitrogen atom, and
R$^1$ and R$^2$ are identical, R$^3$ and R$^4$ are identical, R$^5$ and R$^6$ are identical.

2. The organic semiconductive material according to claim 1, wherein R$^1$ and R$^2$ represent a substituted or unsubstituted alkyl group, a substituted or unsubstituted alkoxy group, a substituted or unsubstituted alkylthio group, or a substituted or unsubstituted aryl group.

3. The organic semiconductive material according to claim 2, wherein R$^1$ and R$^2$ represent a substituted or unsubstituted aryl group.

4. The organic semiconductive material according to claim 1, wherein R$^3$ to R$^6$ are each independently a lower alkyl group or a hydrogen atom.

5. The organic semiconductive material according to claim 1, wherein R$^3$ to R$^{10}$ are all hydrogen atoms.

6. The organic semiconductive material according to claim 1, wherein R$^1$ and R$^3$ are bonded to each other to form a ring, and R$^2$ and R$^4$ are bonded to each other to form a ring.

7. The organic semiconductive material according to claim 6, wherein R$^1$ to R$^4$ independently represent a substituted or unsubstituted alkylthio group.

8. An organic electronic device, comprising
a charge-transporting member comprising an organic semiconductive material represented by formula (I):

wherein:
R$^1$ to R$^{10}$ independently represent a hydrogen atom, a substituted or unsubstituted alkyl group, a substituted or unsubstituted alkoxy group, a substituted or unsubstituted alkylthio group, or a substituted or unsubstituted aryl group, optionally bonded to each other to form a ring; and X is a carbon atom or a nitrogen atom, and $R^1$ and $R^2$ are identical, $R^3$ and $R^4$ are identical, and $R^5$ and $R^6$ are identical.

9. The organic electronic device according to claim 8, wherein the charge-transporting member is an organic semiconductive layer, and the organic electronic device is an organic thin film transistor.

10. The organic electronic device according to claim 9, further comprising:
- a pair of a first electrode and a second electrode, both separated from each other with the organic semiconductive layer existing therebetween; and
- a third electrode,
- wherein a current running through the organic semiconductive layer between the first electrode and the second electrode is controlled by adjusting the voltage applying to the third electrode.

11. The organic electronic device according to claim 10, further comprising an insulating film between the third electrode and the organic semiconductive layer.

12. A display device, comprising a display element equipped with an organic electronic device, wherein:
- the display element is driven by the organic electronic device, and
- the organic electronic device comprises a charge-transporting member comprising a crystalline organic semiconductive material which is a herringbone packing, represented by formula (I):

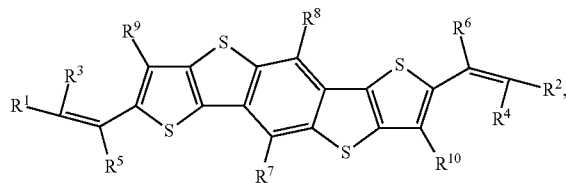

wherein:

$R^1$ to $R^{10}$ independently represent a hydrogen atom, a substituted or unsubstituted alkyl group, a substituted or unsubstituted alkoxy group, a substituted or unsubstituted alkylthio group, or a substituted or unsubstituted aryl group, optionally bonded to each other to form a ring;

X is a carbon atom or a nitrogen atom, and $R^1$ and $R^2$ are identical, $R^3$ $R^4$ are identical, and $R^5$ $R^6$ are identical.

13. The display device according to claim 12, wherein the display element is at least one selected from the group consisting of a liquid crystal element, an electroluminescence element, an electrochromic element, and an electrophoretic element.

* * * * *